(12) United States Patent
Hoang et al.

(10) Patent No.: US 11,344,009 B2
(45) Date of Patent: May 31, 2022

(54) ALL STERILE MALES OF CULICINE MOSQUITOES: A METHOD OF CREATION

(71) Applicant: Duong Thanh Hoang, Hanoi (VN)

(72) Inventors: Duong Thanh Hoang, Hanoi (VN); Kim Phuc Hoang, Oxford (GB)

(*) Notice: Subject to any disclaimer, the term of this patent is extended or adjusted under 35 U.S.C. 154(b) by 268 days.

(21) Appl. No.: 15/318,408

(22) PCT Filed: Jul. 7, 2014

(86) PCT No.: PCT/VN2014/000004
§ 371 (c)(1),
(2) Date: Dec. 13, 2016

(87) PCT Pub. No.: WO2016/007975
PCT Pub. Date: Jan. 4, 2016

(65) Prior Publication Data
US 2017/0112110 A1  Apr. 27, 2017

(51) Int. Cl.
| A01K 67/033 | (2006.01) |
| C12N 15/113 | (2010.01) |
| C12N 15/11 | (2006.01) |
| C12N 15/85 | (2006.01) |

(52) U.S. Cl.
CPC ........ *A01K 67/0339* (2013.01); *C12N 15/111* (2013.01); *C12N 15/113* (2013.01); *C12N 15/85* (2013.01); *A01K 2207/05* (2013.01); *A01K 2217/05* (2013.01); *A01K 2217/20* (2013.01); *A01K 2217/206* (2013.01); *A01K 2227/706* (2013.01); *A01K 2267/02* (2013.01); *C12N 2310/14* (2013.01)

(58) Field of Classification Search
CPC .................................................. A01K 67/0339
See application file for complete search history.

(56) References Cited

U.S. PATENT DOCUMENTS 7,868,222 B1    1/2011    Dobson

FOREIGN PATENT DOCUMENTS

| WO | 2001039599 A1 | 6/2001 |
| WO | 2012129577 A1 | 9/2012 |
| WO | 2014089581 A1 | 6/2014 |

OTHER PUBLICATIONS

Boisson et al. (2006, FEBS Letters, vol. 580, pp. 1988-1992) (Year: 2006).*
McGuire S.E. et al. Gene expression systems in *Drosophila*: a synthesis of time and space, Trends Genet., 2004, 20(8), p. 384-91, Figure 2.
Fu G. et al., Female-specific insect lethality engineered using alternative splicing, Nat. Biotechno., 2007, 25(3), p. 353-7.
Galizi R. et al., A synthetic sex ratio distortion system for the control of the human malaria mosquito, Nat. Commun., Jun. 10, 2014, 5: 3977.

* cited by examiner

*Primary Examiner* — Thaian N. Ton
*Assistant Examiner* — David A Montanari
(74) *Attorney, Agent, or Firm* — Jeffrey S. Melcher; Melcher Patent Law PLLC

(57) ABSTRACT

An all male Culicide mosquito population is created by knocking down its Transformer-2 gene, causing the dysfunction of X chromosome-bearing sperm, hence producing severe biased male progenies. Unlike previous methods, we recently discovered that the Tra-2 knockdown also results in female-specific zygotes lethality (XX). This art is therefore also designed to kill early female zygotes (XX) that may have survived the previous knockdown, and the all male progenies are created only when an antibiotic substance has been added into food and drink to feed mosquitoes. The strict limit of the antibiotic exposure time allows mosquito-adapted *Wolbachia* bacteria to survive. Selected *Wolbachia* bacteria may induce cytoplasmic incompatibility (CI) of up to 100%. All the progenies are therefore genetically males, which cause sterility when outcrossing with females infected by another *Wolbachia* strain (bidirectional CI) or are uninfected (unidirectional CI) in natural environment.

14 Claims, 2 Drawing Sheets

Specification includes a Sequence Listing.

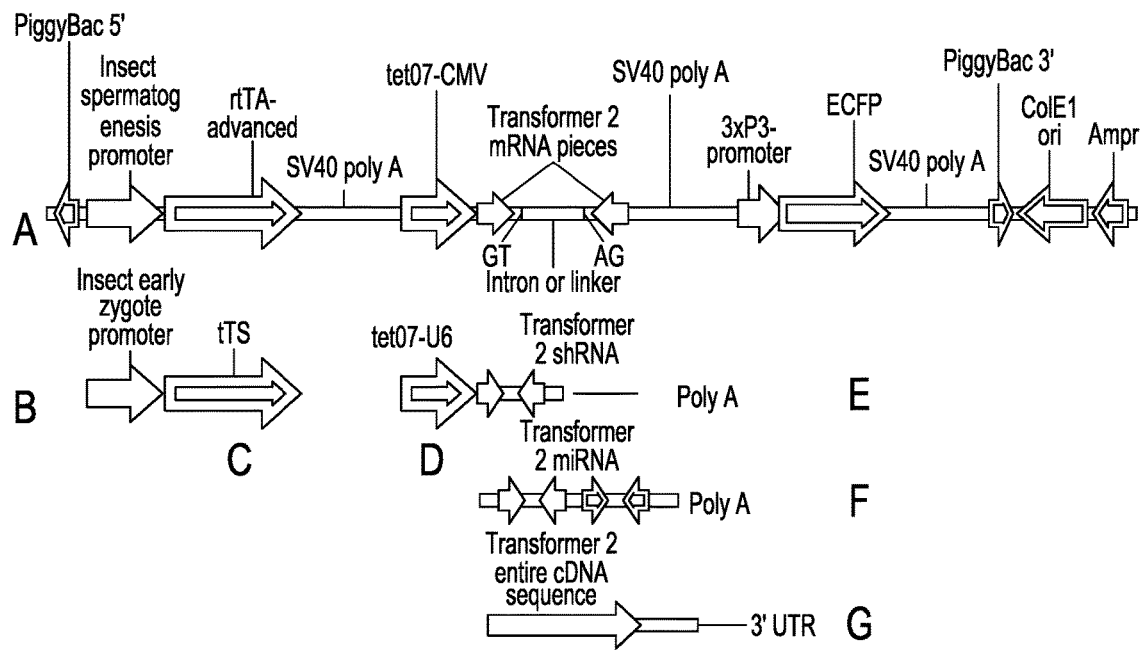

Figure 1. The components in vertically parallel positions can be exchanged to assemble different Tet-on+Tra-2 RNAi constructs. A. Schematic representation of a completed Tet-ON+Tra2-RNAi system which produces long dsmRNAs; B. An insect early zygotic promoter can be used to express trans-activator protein; C. tTS can be exchangeable for rtTA in different genetic backgrounds; D. Insect U6 minimal promoter can be used to express sort hairpin RNA and miRNA; E. shRNA structure; F. micro RNA structure; G. entire Tra-2 cDNA can be used to overexpress Tra-2 protein.

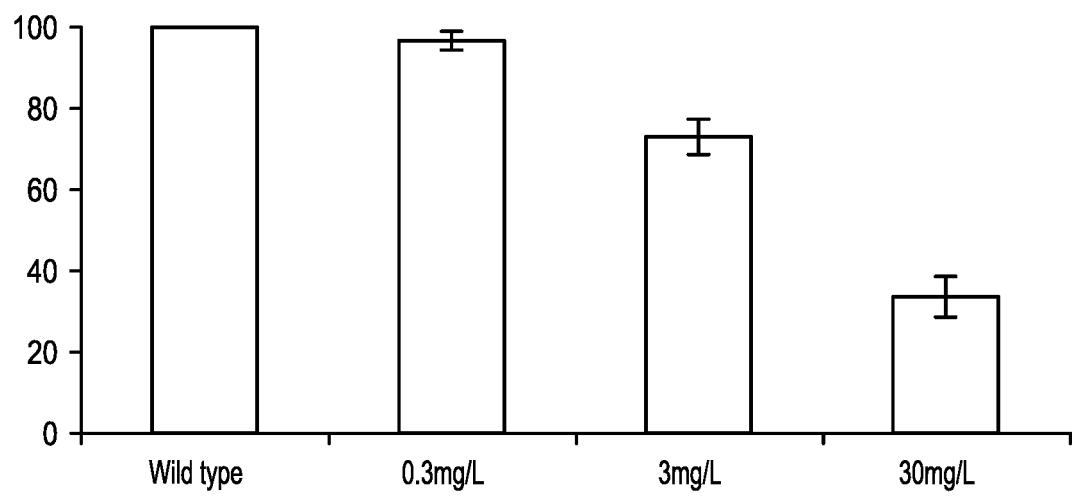
Figugre 2. Tra-2 knockdown level in a Tet-on transgenic line inducing by different Dox concentrations (The results where derived from experiments in example 10).

ALL STERILE MALES OF CULICINE MOSQUITOES: A METHOD OF CREATION

SEQUENCE LISTING

The instant application contains a Sequence Listing which has been submitted electronically in ASCII format and is hereby incorporated by reference in its entirety. Said ASCII copy, created on Apr. 21, 2021, is named 17134_SL.txt and is 18,925 bytes in size.

BACKGROUND OF THE INVENTION

One method invented to control insect populations is named the "sterile insect technique" or SIT and this has been seen as an effective, species-specific and environmentally friendly method for controlling pest populations. The SIT method creates sterile male insects through the use of radiation or chemical sterilants and releases them into natural habitats where the males would instinctively look for natural females to mate with. When a huge number of sterile males are released over an extended period of time, it can cause the natural insect population to collapse, or even become extinct[1-3].

The example of SIT has seen the successful elimination of the New World screwworm, *Cochliomyia hominivorax*, from the southern states of the USA, Mexico and all of Central America[4].

The insect created by the SIT method needs to have undergone a sexing step to remove the females; this is because many insect species containing sterile females if released would look for blood meals and may transmit diseases (in the case of mosquitoes) or damage fruits (in the case of med fly)[5].

To physically separate male insects from a release population is, however, too labour-intensive; furthermore, to do so can damage small insects such as mosquitoes (Unpublished data). In another approach to sexing in silk worms, the translocated chromosome fragments were linked to gene encoding for different egg colours in the sex chromosomes, but there is no such marker in mosquitoes[6-7].

The mutant strains created by radiation or chemicals are usually accompanied with a significant decline in male mating competitiveness in comparison with wild type males, which can result in failures in vector control strategies involving the release of male mosquitoes. The greatest concern for society at the moment is that the insect genetic modification technique is not yet advanced enough to be used as a replacement method for SIT. This is due to unanticipated consequences of transgenes that move into wild mosquitoes via fertile matings. Once this occurs, remediation of any untoward effects becomes extremely difficult—even impossible—to revert[5].

Mosquito releases have been performed in many SIT trials. In these cases, although the programs were not of sufficient scale to be effective in non-isolated areas, modest effects on the sterility of eggs laid and the density of wild-population were generally observed. This failure was attributed to three major factors: (1) the production of males is not enough for release, due to absence of sexing strains; (2) loss of male fitness and (3) immigration into release areas; these problems would seriously need to be addressed before any new SIT trial could be continued[5].

Modification of SIT was also performed by the use of *Wolbachia*-induced cytoplasmic incompatibility (CI) against *Cx. quinquefasciatus* in Myanmar. CI occurs when a *Wolbachia* infected male mates with a female that is infected by another *Wolbachia* strain (bidirectional CI) or is uninfected (unidirectional CI). This project used male mosquitoes sterilized by CI and quickly eliminated an isolated population of *Cx. quinquefasciatus*[8]. Although this seems to be a very effective method for vector control, it is very costly to remove a large number of females before a big-scale release program. Furthermore if there are not enough males for release in a non-isolated region, the control program would certainly fail.

O Neill discloses a method to transinfect new *Wolbachia* into mosquitoes in which the *Wolbachia* doesn't naturally colonize, inhabit or reside[9]. This method includes the step of culturing the *Wolbachia* in mosquito cell lines and injecting it into mosquito embryos. This new transinfection method claims to protect the host from pathogens as well as modifying a number of biological characters of the host. To carry out this method as a vector control application, the inventors need to release female mosquitoes into the natural habitat because *Wolbachia* occurs in maternity transmission only.

Dobson discloses a micro-injection method to transinfect new *Wolbachia* into mosquitoes by embryo cytoplasmic transfer from host to non-host species embryos[10]. The art used CI as a tool for mosquito control when releasing *Wolbachia* infected males into a mosquito population where the *Wolbachia* doesn't naturally colonize, inhabit or reside. The art requires to mechanically removing females before release.

Methods of transformation of insect species with foreign DNA were disclosed by Asburner et al.[11]. These methods paved a new way to produce transgenic species.

DeVault et al.[12,13] invents a two-stage process which improves the SIT procedure; Insects are sexed by expression of a lethal gene linked to a stably inserted female specific promoter. This system succeeds in killing females and producing an all-male population. The males can then be sterilized by irradiation or chemical treatment and released into the environment, however, sterilizing males through irradiation or chemical treatment can cause significant loss of male fitness, which means that a much larger number of insects can be released than those predicted by simple models. 50% of the mosquito population is females; this art is designed to kill females thereby producing only half the number of progeny, in comparison with an art which produces 100% males.

Bello et al.[14] evaluates the efficiency of the Tet-off tetracycline regulated gene expression system in *Drosophila* by the generation of transgenic lines expressing a tetracycline controlled transactivator protein (tTA), with specific expression patterns during embryonic and larval development. The conditional expression of Antp has a lethal effect in *Drosophila* embryos. The authors show that the expression of a gene placed under the control of a tetracycline-responsive promoter can be tightly monitored both spatially by the regulatory sequences driving the expression of tTA and temporally by tetracycline. This provides the basis of a versatile binary system for controlling gene expression in insect and potential applications.

To avoid radiation damage, a new method named RIDL (Release of Insects carrying a Dominant Lethal) has been patented[15,16]. The RIDL causes lethality resulting from a dominant lethal gene and exploits a tetracycline-repressible transactivator (tTA) to control expression of the gene which is similar to those Bello used (see example above). The regulatory system of the dominant lethal gene requires a Tet-off system. Permissive conditions are maintained by the presence of Tetracycline or Doxycycline (substances) in the lab-rearing conditions. If the substances are removed, the system will be activated and cause lethality. Highly efficient repressible RIDL systems were first demonstrated in *Drosophila* models and in the Mediterranean fruit fly. In *Aedes* mosquitoes, RIDL has been proved to be efficient, and the males created haven't shown any reduced fitness when compared with wild type males[17,18].

The progress of the RIDL field trials is however being met with stiff resistance by many residents and environmentalists alike, who are uncomfortable with releasing millions of genetically-modified mosquitoes (of which 0.5% in each trial are females, due to being misidentified as males in the sexing step) into their backyards. Moreover, approximately 3% of RIDL offspring can survive even in the absence of Tetracycline (Tet) or Doxycycline (Dox); which highlights the risk of the unanticipated consequences of transgenes entering wild mosquitoes via fertile matings[19].

Use of the Tet-off system for biocontrol has also been reported simultaneously with the RIDL system by Heinrich and Scott[20] using *Drosophila* as a model system to achieve female-specific lethality, wherein the yolk protein 1 (Yp1) promoter was used to drive female-specific tTA, and link the TRE enhancer to the cell death gene, head involutiondefective (hid).

Fu et al.[21] combined the RIDL system and an endogenous female-specific Actin-4 promoter derived from *Aedes aegypti*. The over expression of tTA protein in flight muscles is regulated by the Tet-off system and causes females to be flightless. The sexing problem was addressed and surviving male offspring could pass the transformant genes into the next generation, however, this method has its shortcomings; males also carrying the flightless system and reared on a tetracycline-free diet, spent 21% less time in flight than their wild male counterparts[22]. Moreover, when large numbers of flightless females remain on the water's surface, their bodies and leg movements can prevent eclosion of other males causing them to eventually drown. Because of this, in an industrial insectary, rearing at high density is the only option. Furthermore, the transformant males passing genetically modified materials into the natural population is perceived as a breach of Cartagena Protocol bio diversity guidelines.

Hoang and Hoang[23] disclose a method to genetically produce an all-male population of Culicine mosquitoes. The patent application exploits our findings about the Transformer-2 gene in Culicine mosquitoes; specifically that the knockdown of this gene has resulted in lethality of X chromosome bearing-sperms. In this case, we suggested driving the Tra-2 RNAi genetic construct by an early spermatogenesis specific-promoter (for example $\beta 2$)[24]. The RNAi will be distributed to all spermatocytes and spermatids via the cytoplasmic bridges; hence no X chromosome-bearing sperm will survive. All males created by that method are fertile and the genetic system is thereby regulated by the Tet-off system; in which the absence of the substances activates the sperm killing (hence producing all males). Genetic sexing strains created by this method can be directly used for a vector control strategy by producing an all-male population. In brief, this method ensures a male only population producing no female progeny, only viable male progeny. When such Tra-2 RNAi genetic construction is controlled by a tetracycline-repressible transactivator and linked to Y chromosome, it would produce a super Mendelian segregation and an artificially conditional meiotic drive system is established. In fact, this method exploited the discovery of Tra-2 regulatory mode to create an artificial Meiotic Drive system. Insertions located in other chromosomes also result in all-male offspring as the substances are removed. This system can knock down a target population in a relatively short time-frame. Sex biased ratio appears in the absence of the substances.

This method suffers from an undesirable drawback which has been subject to debate for long time; namely that when released it may result in extinction of a population or even an entire species due to its self-driven mechanism. Under this Meiotic Drive method, genetically modified materials will be passed on into the natural population and the Cartagena Protocol may be violated.

Use of the Tet-on system for practical application of biological control has not been performed yet. In this 'Tet-on' system, gene expression is dependent on the presence of doxycycline, which has also been showed in *Drosophila*. Advantages of the system include the more rapid control of the transgene induction, as the Tet-off system can takes days to clear Tet or Dox from the organism[14,25].

In a further aspect, if there is a requirement to recombine the above mentioned RIDL or the other genetic sexing systems with *Wolbachia* for inducing CI sterilization, practicability would be extremely difficult, because it is impossible to maintain an insect line in lab-permissive conditions with the presence of Tet or Dox (Tet-off system) without killing the endosymbiotic bacteria of insects[26].

There is a need in the art of mosquito control which uses the methods outlined, whilst avoiding the problems mentioned above.

The present invention offers a method to overcome such problems.

SUMMARY OF THE INVENTION

The present invention develops a method to create an all sterile male population of Culicine mosquitoes. This Tra-2 RNAi system is operated by an Tet-on system. All-male mosquitoes are only created after a substance being fed to a Transformer-2 knockdown genetic system bearing strain, which is also trans-infected to bear one or more different *Wolbachia* endosymbiotic bacteria (s). The selected *Wolbachia* are different from those which may be already resident in the natural mosquito population. The males cause sterility after interbreeding with wild females and can be directly used for mosquito control strategies.

This invention exploits two discoveries: 1) X chromosome-bearing sperms are killed when the Tra-2 gene is knocked down (Hoang and Hoang, 2012)[23]. This finding was used in combination with the Tet-off system to create an all male progeny population[23]. However, the drawback of this system is a self-driven and if linked to Y chromosome, it would drive population to extinction. We used that system[23] here in combination with Tet-on to collect all male progenies with inactive Tra-2 RNAi system; 2) We have recently discovered that early female zygotes (XX) were also killed as Tra-2 gene is knocked down in Culicine mosquitoes. The first discovery has been previously used to develop a method to genetically produce the all-male populations of Culicine mosquitoes mentioned above[23]. Key differences to the previous art is that in the regulatory system for this genetic method, we design the killing effect to appear only in the presence of the substances (Tet-on system) and the female-specific killing effect is also expressed in early zygote stages. The substance of the Tet-on system is Doxycycline only, which means that the permissive conditions in this method are free from the substances, and all male offspring would appear only when the substances are being fed into the transformant insects. This strategy doesn't require a continuous maintenance in Dox condition for a genetic sexing strain. The Tra-2 knockdown genetic system controlled by a Tet-on system expresses only in the presence of Dox, so the transgenes will be silenced in natural environment.

All methods using the Tet system before this invention have exploited the absence of Tet or Dox from the natural environment, activating mosquitoes genetic lethal systems in the natural environment via the Tet-off regulatory mechanism. Continuous maintenance of the genetic strains in the antibiotic in laboratory condition before release also means that no bacteria (such as the endosymbiotic *Wolbachia*) can survive in the organisms, moreover, if the goal is to achieve only one sex of offspring just before using such offspring for a certain purpose, the art of regulation can be achieved by the use of an oppositely regulatory system (Tet-on system). In such circumstance, the substances are only required when the trans-activator of the genetic system activates and users want to collect the desired sex in offspring. This strategy would therefore reduce the cost of the substances being added to the food. Furthermore, this method also reduces the risk of Dox contamination into the natural environment, via wasted food or rearing medium, which would cause greater microbial antibiotic resistance.

The insects in this invention produce their progenies in a normal sex ratio in either a laboratory or the natural environment under no Dox conditions, hence the Tra-2 knockdown genetic system is silent and does not produce genetically modified proteins which are claimed to be a risk for food chain contamination. Dox is present in conditions that do not occur in the natural environment of the organism. The addition of the controlled conditions permits expression of the Tra-2 knockdown genetic system. X chromosome-bearing sperms and early female zygotes are specifically killed as the Tra-2 knockdown genetic system activated hence producing all males.

The second most important art of this invention is that in the Tet-off system, insects must be continuously fed on Tet or Dox. Long term exposure of a genetic sexing strain insect to the antibiotic would remove all endosymbiotic bacteria that the insects may contain. Some *Wolbachia* in *Aedes albopictus* can tolerate a higher concentration of antibiotic, but this is not typical of other insects[26]. The Tet-on system applied for this Tra-2 RNAi system only requires the presence of Dox between the third larval stage at the start of spermatocyte formation and in the adulthood stage at the last generation, in order to create an all-male progeny, meanwhile *Wolbachia* removal by antibiotic insect treatment requires at least one discrete generation to be treated. The substance concentration for activating and maintaining a Tet-on system is in a huge range from 1 mg/L to 1000 mg/L[25]. For a Tra-2 Tet-on system we created, 30 mg/L significantly induced knockdown within 12 hours (see more in examples). Meanwhile, to remove *Wolbachia* from insects needs 125 mg Tet/L for two discrete generations in Drososphila[27] and up to 5000 mg/L for one generation in *Aedes albopictus*[26] (between 10-15 days). The *Wolbachia* of Tet-on maleness offspring are therefore safe with the limit exposure time in which it needs 2-3 days in larvae-pupae stages and two days in adults.

If the *Wolbachia* in the male insect is absent or different to those in the natural population of the species, it induces cytoplasmic incompatibility (CI). There are a number of publications reporting approx. 100% CI and maternity transmission after a new *Wolbachia* transinfected mosquito line established[28,29]. A suitable *Wolbachia* can cause a complete CI and sterilize all wild females with which the males mated. The Tra-2 knockdown system/Tet-on males can simply be crossed with the desired infected females to establish a genetic sexing line carrying *Wolbachia*, which causes a complete CI when interbreed with wild females. A Tra-2 knockdown system/Tet-on strain can also be used as material to transinfect a desired *Wolbachia* via a direct adult micro-injection method.

The males from this invention can be used in population control; they don't pass on the genetic system through mating, and they can also potentially compete with wild type males in mating. Distribution of the "Tra-2 knockdown system/Tet-on plus *Wolbachia*" males into the environment starts a mosquito biological and genetic control method, but there is no risk of this system escaping into the natural population of mosquitoes.

In a further aspect, a Tra-2 knockdown system/Tet-on strain can also be used for irradiation or chemo-sterilization for sterility. This provides a new exit for SIT in mosquitoes. This strategy reinforces the sterility in case CI is not completed (100%) in certain combinations between mosquitoes and *Wolbachia* lines.

The sterile males can be used to control their own species but in allopatric distributions of closely related species, these males can interbreed with females of the other species, which may result in sterility, due to post-mating reproductive isolation. This can be performed between *Aedes aegypti* and *Aedes albopictus*, as no natural introgression between these species has been reported so far.

Through the development of this invention, we do not rule out the possibility of using male mosquitoes created by the Tet-off regulation[23]. The use of Tet-off regulation to express a lethal gene in all development stages as RIDL completely limits genetic lines carrying *Wolbachia* in the presence of the antibiotic. In the method disclosed by Hoang and Hoang[23], a spermatogenesis specific-promoter is used to drive the expression of tTA gene to regulate the transactivator system. This specific promoter has advantages over other promoters in that it only needs limited time to be in permissive conditions, (between the third larval stage as the start of spermatocyte formation and adulthood stage). However, these conditions need to be repeated in every generation resulting in high risk for *Wolbachia* they carry. The *Wolbachia* density in the insect plays a crucial role in the CI level that it may cause. Exposure to antibiotics in every generation would reduce the *Wolbachia* density and CI. Fertile males can be created and carry the Tra-2 RNAi/Tet-off system into natural environment. Using a *Wolbachia* trans-infected line as a background material to transform the Tra-2 RNAi/Tet-off system requires PCR to check the *Wolbachia* presence in a number of samples from every generation. A solution for this is to cross the Tra-2 RNAi/Tet-off males with desired *Wolbachia* trans-infected females in the last generation before release. This requires an extra sexing step to remove *Wolbachia* trans-infected males from the females before the cross. Both cost and time are considerably increased when compared to using a *Wolbachia* trans-infected line to transform the Tra-2 knockdown system/Tet-on strain (when users need to collect all males in this method, the substances will be simply added to the food to feed the trans-infected and transformant lines).

We have now discovered a new method for mosquito control, applicable to different insects and Culicine mosquitoes. Any insect having a Tra-2 genetic similarity to those found in *Aedes albopictus, Aedes aegypti* or *Culex* spp i.e., killing X chromosome-bearing sperms and early female zygote when their Tra-2 knockdown, can be subjected to this method. The combination of a Tra-2 knockdown genetic system/Tet-on strain and the complete *Wolbachia*-induced CI produces all-sterile males for a control program. Irradiation or chemical sterilants provide an alternative option, when not using *Wolbachia*-induced CI or CI is not completed. Although the drawback of using irradiation for further sterilization after a sexing step, it offers a firm barrier against passing on genetically modified materials into the natural environment. The Tra-2 knockdown genetic system/Tet-on provides 100% males in half the time, when compared to the one sex killing method in which 50% of progeny is lethal and only half of desired sex remains [12,13,21]. This genetic system can therefore be optionally used together with irradiation or chemical sterilants The RIDL and the other mentioned sexing systems must express their genetic system in the natural environment to complete the task of killing one or both sex. Their only option is to use Tet-off in their regulatory system. The permissive conditions allowing a stock of organisms to be normally bred in the lab condition are toxic for *Wolbachia*, therefore making a combination of the two in one both costly and difficult. The use of antibiotics is also costly and may potentially increase antibiotic resistance in the natural environment. The use of Tet-on system in this invention doesn't require the regular presence of the substances and therefore *Wolbachia* can be combined to induce CI sterilization. It discloses a cheaper, safer and more convenient method for insect biological control.

BRIEF DESCRIPTION OF THE FIGURES AND SEQUENCES

In FIG. 1, the components in vertically parallel positions can be exchanged to assemble different Tet-on+Tra-2 RNAi constructs. Schematics illustrated the creation of A. Tra-2 long dsmRNAi constrtuct; E. Tra-2 shRNA construct; F. Tra-2 miRNA construct and G. Multiple Tra-2 construct to overexpress the gene. All the constructs were trans-activated by Tet-On mechanism[30]. B. An insect earyly zygotic promoter can be used to express trans-activator protein. C. rtTA or tTS can be optionally used depending on each case. D. This led to the use of pTre-tight or pTre-mod/U6, respectively.

In FIG. 2, the Tra-2 knockdown level in a Tet-on transgenic line inducing by different Dox concentrations (The results were derived from experiments in example 10).

```
                                            SEQ ID: No 1
CAAGACGAAGGTTTCCCGAGGGTTCGGATTCGTGTACTTCCAGGAACAG

AGTGCGACCACCGAAGCCAAAATGCAGTGTAATGGAATGATGCTGCATG

AGCGCACGATTAGAGTGGATTATTCGGTGACCGAAAGACCGCATACGCC

CACGCCCGGTGTCTACATGGGAGCTAGAAGCACTGAGAAACGGAAGCAC

CGCAGTTCCTATAGCTACAGGAGACGGAGCTATGATGACGATTACCATC

ATCGGCGGTCAAGACGCAGCAGATCTCGTTCCTGTCATCATCACCGTAG

ATCTAGTCATCGCCATCACCATCGACGTGACCGTGCTCGTGATCGTTCT

CCATCTTATTCCTCAGTTGACTCACGTCGATCCTATCGATAATGTGCTA

GAAGGATTGTGTTTTTGACGTAAGTCATCTTTTTCAAGACCTCACGAAG

ACCCTACAAACAAAGAAGTTCAAGTCAAGTATTATTGAAGATAGAATCT

GTATCAGTAAAAACTATTCTTCAAATGACACAAGGGAAGAACAGATTAC

TCTTCATTAATCCAAGGGTAAATTGTATGTAGCTAACCGTTCTGTTTTT
```

```
                                            -continued
CTTTTCGTTTCAGGATGTTTGGATTTCTTCACATTTTAGAGAACTAGTT

TTCATTATTCCGCGATTCAAACTAAACATTTTATTTATTTATTAGTTAA

AGATCGTGTGGTTATGAAATGTCGTTTGTGCAACCATTAACCAAAATA

AGGGATTGCTAAAAAAAAA
```

```
                                            SEQ ID: No 2
TGCCAAGACGAAGGTTTCCCGTGGGTTCGGATTCGTGTACTTCCAGGAG

CAGAGTGCGGCCACCGAAGCCAAAATGCAGTGCAATGGGATGATGCTGC

ATGAGCGCACGATTAGAGTGGATTATTCGGTGACCGAAAGACCGCATAC

GCCCACGCCCGGTGTCTACATGGGAGCTAGAAGCACTGAGAAACAGAAG

CACCGCAGTTCCTATAGCTACAGGAGACGGAGCTATGATGACGATTACC

ATCATCGGCGGTCAAGACGCAGCAGATCTCGTTCCTGTCATCACCATCG

TAGATCTAGTCATCACCATCGCCATCGACGTGACCGTGCTCGTGATCGT

TCTCCATCTTATTCCTCAGTTGACTCACGTCGATCCTATCGATAATGTG

CTAGAAGGATTGTGTTTTTGATGTAAGTCATCTTTTTCAAGACCTCACG

AAGACCCTACAAACAAAGAAGTTCACGTCAAGTATTATTGAAGATAGAA

TCTGTATCAGTAAAAACTACTCTTCAAATGACACAAGGGAAGAACAGAT

TACTCTTCATTAATCCAAGGGTAAATCATATGTAGCTAACCGATCTGTT

TTTCTTTTCGTTTCAGGATGTTTGGATTTCTTCACATTTTAGAGAACTA

GTTTTCATGGTTCCGCGATTCAAACTAAACATTTTATTTATTTATTAGT

AAAAGATCGTGTGGTTATGAAATGTCGTTTGGGCAACCATTAACCAAAA

ATAAGGGATTGCTAAAAAAAAA
```

Sequence ID1 is a Tra-2 mRNA found in males at a high frequency meanwhile Sequence ID2 is a Tra-2 mRNA dominantly found in females. Sequence ID1 was used to create the construct to transform multiple Tra-2 loci into *Aedes* genome.

DETAILED DESCRIPTION OF THE INVENTION

The Tra-2 knockdown genetic system in the present invention contains the Tra-2 RNAi core structure, which is similar to those disclosed in our prior invention[23] but they are contrasting in the regulatory components, which opens new exits for a combination of the Tra-2 knockdown genetic system with the other existent concepts. In this invention, a Tet-on system is used to trans-activate the Tra-2 knockdown genetic core structure. And in this invention, the female-specific killing effect is designed to express not only in X chromosome bearing sperm but also in early zygote stages by different promoter. A genetic strain created by this invention may also contain different promoters or other genetic knockdown systems.

Hoang and Hoang[23] found that the knockdown of Tra-2 gene in Culicine mosquitoes causes X chromosome-bearing sperms lethality. We have recently discovered that Tra-2 knockdown also results in early female zygote (XX) lethality. These female zygotes were created from some X bearing sperms which were survived from the knockdown during spermatogenesis. We designed to use a specific early zygotic promoter to knockdown Tra-2 and kill the early zygotic females. This method is not required for all the cases, depend on the insertion site of RNAi construct and species, some Tra-2 RNAi genetic sexing strain could kill up to 100% X bearing sperms during spermatogenesis meanwhile others left some female survivors. This invention discloses the use of an insect spermatogenesis specific promoter to regulate the Tet-on system, which causes X chromosome-bearing sperms lethality in the presence of substance. At the same time, we exploit an insect early zygote specific promoter to drive the Tet-on system. This produces a female killing effect into any escaped X chromosome-bearing sperm which may survive from the prior spermatogenesis knockdown and fertilizing embryos. This killing also occurs in the presence of substance only.

A Tra-2 knockdown genetic system in this invention can be defined as the genetic techniques by which the expression of organism's Transformer-2 genes are reduced. The knockdown agent can be the expression of one or more Tra-2 RNAi genetic constructs [long DsRNA (siRNA), shRNAs][31] which produces double looped mRNA strands with a minimal length of the complementary part which can be less than 19 base pairs. The knockdown agent can be the expression of one or more microRNA (miRNA) genetic constructs, in which the complementary part is derived from 3' UTR or 5'UTR sequences of mRNA Tra-2 gene. In a further aspect, the knockdown of Tra-2 gene can be a result of an overexpression by transformation of many copies of the gene containing the entire Tra-2 transcribed region, and the as well as flanking regions of about 1000 nt downstream to it. The Tet-on regulatory part can be adhered to a desired promoter of the Tra-2 transformant locus and Doxycycline will be used to induce an overexpression of this gene. In this invention, a creation of a genetic construct which transcribes long DsRNAs (siRNA) in the presence of Dox is disclosed in detail, but we not rule out the practicability of the above mentioned techniques, which can be used to silence the Tra-2 gene and result in female specific killing.

The Tra-2 knockdown genetic system in the present invention may be any part of Tra-2 encoding sequences (mRNA) of Tra-2 genes originated from *Aedes albopictus, Aedes polynesiensis, Culex quinquefasciatus* or the other Culicine mosquitoes which are capable of producing a knockdown (interference) effect to the Tra-2 gene of the respective species. We do not rule out the possibility that a Tra-2 RNAi system containing Tra-2 recombinant sequences from certain. Culicine mosquito species can also cause a knockdown (interference) effect to the other closely related mosquito species within the subfamily Culicine. 3' UTR or 5'UTR sequences of mRNA Tra-2 gene are not ruled out in case they be used in a miRNA genetic structure to silence the gene. Any insect displaying a Tra-2 genetic similarity to those found in *Aedes albopictus* or *Aedes aegypti* i.e., killing X chromosome-bearing sperms and early female zygote when their Tra-2 knockdown can be subjected to this method.

In this invention, a Tet-On Advanced transactivator (Clontech) is firstly designed to be controlled by an insect spermatogenesis specific promoter. An unlimited number of promoter candidates can be selected for this driver (Bam, nanos, aly and β2)[24]. This complex is followed by an integrated TRE-based expression vector (e.g., pTre-Tight), which expresses the Tra-2 knockdown genetic system in the presence of the system's inducer, doxycycline.

The killing effect into X chromosome-bearing sperms is preferable at more than 90%. In the best circumstance of the system, 100% X sperms is lethal, hence producing 100% male progeny. The X sperm killing effect depends on a combination among an inserted position of the Tra-2 knockdown system in genome and the ectopic expression of the selected promoter in the genetic background of a targeted species. A genetic strain which produces less than 100% male progeny is subjected to a second Tra-2 knockdown system, in which the Tet-On transactivator is driven by an early zygotic promoter. We prefer that all early female zygotes are killed in embryos or very soon after they hatch. An early zygotes promoter is used for this Tra-2 knockdown, for example AaKLC2 promoter or its orthologs[32]. We don't rule out that other insect early zygotic promoters can be used in this invention.

The Tra-2 knockdown system disclosed in this invention can therefore reside in one or different chromosomes. In the case of using long DsmRNAs (siRNA) to silence Tra-2, the RNAi core structure is similar but promoters for driving a Tet-On transactivator can be different for spermatogenesis or early zygotic expression. If the miRNA technique is chosen to silence the Tra-2 gene, 3'UTR or 5'UTR sequence of the Tra-2 mRNA can be inserted under a miRNA backbone. This drives the expression of miRNA and doesn't require an ectopic promoter. The overexpression technique uses the same promoters to drive the Tet-On but the core genetic structure are the entire Tra-2 transcribed region, and about 1000 nt of the flanking regions downstream to it (3'UTR).

The expression of the knockdown systems are specific in the spermatogenesis and possibly extend to early zygotic stages. The Dox induces the Tet-On needs to be presented between the third larval stage when spermatocytes are initially formed to adulthood. Early zygotic knockdown can be induced by collecting eggs on filter paper soaked with Dox at a desired concentration. Three days for conditioning of the eggs on such induced conditions is preferable to kill any X bearing sperm fertilized zygotes which escaped the previous spermatogenesis knockdown. This method saves a huge cost for Dox in comparison to the amount of the antibiotic needed to be used throughout the life cycle for Tet-Off system. This method therefore reduces the risk of Dox resistance of microbes habitat, where wasted rearing medium of insectaries or factories going out.

We prefer to select suitable insect spermatogenesis specific promoters, which can activate the Tra-2 RNAi construct and produce dsmRNAs into all daughter spermatids, hence killing entirely X chromosome bearing sperms. Basically, the different spermatogenesis specific promoters can be used to change a dysfunction ratio of X (n) chromosome-bearing sperms to readjust the sex ratio. These males are genetic males which carry a Y chromosome. In the presence of Dox, males created by this method are not sterile, but they produce only Y chromosome bearing sperms.

We prefer that the Tra-2 knockdown construct can be located on any chromosome, heterozygote or homozygote, one or more loci, however, we can exploit this system differently according to different purposes.

We suggest that a transgenic line containing a single insertion of the transgene can be used as a background for another transformation event. A second transformative event which occurs on the same chromosome as the first one would be especially preferable. The occurrence of two transformation events on the same chromosome would prevent them from being segregated in successive generations, and would be particularly valuable in cases where two or more Tra-2 loci exist in the same species (as in *Aedes albopictus* and *Aedes polynesiensis*) in which two RNAi transformation events are necessary to repress two loci (or alleles).

This invention discloses all of the methods required to create Tra-2 knockdown. DNA constructs, to transform it into insect, and to observe its expression. Production of the constructs can be long dsmRNAs, shRNAs (siRNA) or miRNAs, which have a shared central biogenesis to silence Tra-2. The Tra-2 RNAi system in the present invention may use any part of Tra-2 encoding sequences including 5' and 3' untranslated regions of Tra-2 mRNA gene(s) originated from *Aedes albopictus, Aedes polynesiensis, Culex quinquefasciatus* or the other *Culicinae* mosquitoes and insects which are capable of producing a knockdown (interference) effect to the Tra-2 gene of the respective species. We do not rule out the possibility that a Tra-2 RNAi system containing Tra-2 recombinant sequences from a certain *Culicinae* mosquito species can also cause a knockdown (interference) effect on the other closely related mosquito species within the genus *Culicinae*. This invention scope also applies to any insect species of which their Tra-2 or Tra-2 orthologs knockdown causes X chromosome-bearing sperm and early female zygote lethality, hence having sex determinant genetic similarity with Culicinae mosquitoes. The knockdown can also be obtained by the overexpression due to the transformation of Tra-2 gene copies into the targeted species genome. Finally, a suitable insect spermatogenesis specific promoter needs to be used to drive the tetracycline-regulated trans-activator system to switch the interference effect on and off. An early zygote promoter may be used if required.

In the first approach, the invention uses cDNA sequences derived from the mRNAs of Tra-2 gene in Culicine mosquitoes for DNA manipulation purposes. In the case of using long dsmRNAs or short hairpin RNAs (shRNA), which create siRNAs (19-25 bp) to silence Tra-2, the material to create siRNA core structure is identical to those mentioned in Hoang and. Hoang[23]. The difference is that Hoang and Hoang[23] use Tet-Off to regulate and express the system in the natural habitat of the species, whereas this invention uses Tet-On and the knockdown system is silent in the natural environment.

The Tra-2 gene sequence or its orthologs were obtained as reported in Hoang and Hoang[23]. In detail: putative Transformer-2 encoding gene sequences or their orthologs from *Aedes albopictus, Aedes polynesiensis, Culex quinquefasciatus* or the other *Culicinae* mosquitoes (*Aedes aegypti*) are used as materials to assemble Tra-2 RNAi genetic constructs using recombinant DNA techniques.

The Tra-2 gene sequence or its orthologs can be obtained as an entire mRNA sequence by using RACE or MARATHON kits (clontech).

In 'Examples of this invention', parts or whole RRM (RNA recognition motif) sequences which belong to putative Tra-2 encoding sequences from *Aedes albopictus, Aedes polynesiensis* and *Culex quinquefasciatus* are used. The Tra-2 of *Aedes aegypti* was identified by blastn the *Drosophila* Tra-2A amino acid sequence against the *Aedes aegypti* Genbank database. The outcome was that the AAAEL004293-RA protein belonging to supercontig 1.113 (*Aedes aegypti*-Vectorbase). *Aedes aegypti* is closely related to *Aedes albopictus* and *Aedes polynesiensis*. Primers derived from the AAAEL004293-RA sequence can also be used to amplify Tra-2 sequences of these mosquitoes. The regions with the highest similarity among the orthologous Tra-2 genes are RRMs (RNA recognition motives) which have a length of 240 bp. These primers were tested in many other *Aedes* spp and can successfully amplify these 240 bp regions. We found two RRMs loci (or alleles); each exists in both. *Aedes albopictus* and *Aedes polynesiensis*. They have a 10% amino acid difference from each other and were named SEQ ID: No 1 (RRM1) and SEQ ID: No 2(RRM2) (FIG. 5, Hoang and Hoang[23]). The sequences were deposited in GenBank and the accession number for the RRM sequences are RRM1 (KJ147318, KJ147321, KJ147316 and KJ147314) and RRM2 (KJ147317, KJ1.47320 and KJ147315). In order to knock down these two loci (alleles), it may be necessary to transform different RNAi constructs into each species to repress the respective RRM locus (allele).

A putative Tra-2 gene of *Culex quinquefasciatus* was identified by blasting the *Culex quinquefasciatus* database with the RRM1 and RRM2 sequences. The name of the outcome was CPIJ016646 on supercontig 3.780:5008-5247. The RRMs of the *Culex* Tra-2 gene orthologue was named SEQ ID: No 3 (RRM3) (FIG. 5, Hoang and Hoang[23]). Primers derived from the start and the end of the RRM3 region have been tested for many other *Culex* spp and can successfully amplify these 240 bp regions.

In order to knock the Tra-2 genes down in *Aedes albopictus, Aedes polynesiensis, Culex quinquefasciatus* and the other *Culicinae* mosquitoes by the RNAi technique, three solutions are to be disclosed in the invention.

The first solution is to use SEQ ID: No 1 (RRM1) as materials to create in vitro an RNAi kernel sequence 1. This is a recombinant DNA fragment combining two identical sequences of RRM1, but oriented in opposite directions. The connection between the two RRM1 repeats is a straight intron, or linker DNA sequence. The RNAi kernel sequence 1 is then ligated with transactivator and regulatory elements and a fluorescent marker within a piggyBac plasmid. This plasmid would then be available for transforming into both. *Aedes albopictus* and *Aedes polynesiensis* to knock down their RRM1 locus.

The regulatory element for the kernel sequence is a minimal promoter associated with operator sequences (tetOx7). The minimal promoter plus tetOx7 can be made conditional by using the commercial transactivator regulation systems (Clontech). Gene expression is activated as a result of binding of the tTA protein to tetracycline response elements (TREs) located within the minimal promoter.

For optimal expression, the invention suggests the use of insect spermatogenesis specific promoters to control tTA protein expression. We also prefer to derive a minimal promoter from an insect spermatogenesis specific promoter for controlling the RNAi kernel sequence 1, which helps to eliminate all leakiness. This solution may be applied to any other *Aedes* spp, which has a highly similar RRM sequence in comparison to RMM1, or after obtaining its own Tra-2 RRM sequences by the same pair of primers.

The second solution is to use SEQ ID: No 2 (RRM2) as materials to create an RNAi kernel sequence 2 in vitro. This is a recombinant DNA fragment combining two identical sequences of RRM2, but oriented in opposite directions. The connection between the two RRM2 repeats is a straight intron or linker DNA sequence. The RNAi kernel sequence 2 is then ligated with regulatory elements and a fluorescent marker within a piggyBac plasmid. This plasmid would then be available for transforming into both *Aedes albopictus* and *Aedes polynesiensis* to knock down their RRM2 loci.

In the details, the regulatory elements in the second solution are identical to those described in the first solution. This solution may be applied to any other *Aedes* spp which has a highly similar RRM sequence in comparison with the RMM2, or after obtaining its own Tra-2 RRM sequences by the same pair of primers.

The third solution is to use SEQ ID: No 3 (RRM3) as the material to create in vitro an RNAi kernel sequence 3. This is a recombinant DNA fragment combining two identical sequences of RRM3 but in oriented opposite directions. The connection between the two RRM3 repeats is a straight intron or linker DNA sequence. The RNAi kernel sequence 3 is then ligated with regulatory elements and a fluorescent marker within a piggyBac plasmid. This plasmid would then be available for transforming into *Culex quinquefasciatus*. In the details, the regulatory elements in the third solution are identical as those described in the first and second solutions. This solution can be applied for any other *Culex* spp which has a highly similar sequence of its RRM in comparison, with the RMM3 or after obtaining its own Tra-2 RRM sequences by a pair of primers to be mentioned in Examples. The connective intron or linker between two Tra-2 RRM inverted repeats can be any eukaryotic intron sequence; however, introns from the target species are preferred. The length of connective linker or intron can be from a few to a few hundred nucleotides. We prefer that two nucleotides of GT and AG be inserted at the beginning and at the end of the intron or linker, respectively. These are the strengthening signals for spliceosomes to recognize and to splice out the connective introns or linkers.

Three DNA kernel sequences, Tra-2 RNAi RRM-1, Tra-2 RNAi RRM-2, Tra-2 RNAi RRM-3, are disclosed here as examples of using specific Tra-2 DNA sequences to produce an interference effect into the respective species. The transcription of the DNA kernel structure containing two identical inverted repeats would produce single strands of mRNA, which expose two complementary sequences at their termini. The complementary sequences would bind together forming a double strand hairpin mRNA structure (dsRNAi), in which the looping part is formed by the intron or linker. Mosquito cells recognize the abnormal structure and react by dicing the dsRNA interference in a defence mechanism, which is followed by destroying intact endogenous single strand Tra-2 mRNAs[33,34]. The Tra-2 gene is, therefore, knocked down.

If the desired knockdown effect is aimed to gain from a shRNA construct, about 19 bp target sequence is selected from Tra-2 or its orthologous mRNA sequences, ruling out 5' and 3' mRNA untranslated regions. Instead of rtTA protein produced by the Tet-on advance to regulate long dsmRNA transcription, a transcriptional silencer fusion protein (tTs or tTR) is created by a commercial plasmid (PT3813-5 Clontech) to regulate the operator of the shRNA locus. We prefer that U6 promoter sequence from the modified Tet-responsive promoter (pTremod/U6) derived from the pTremod and the human U6 promoter in the plasmid (PT3811-5 Clontech) would be replaced by U6 insect closely related or specific promoter which is correspondent to the target species.

If the desired knockdown effect is aimed to gain from a miRNA construct to be the case, 19 to 25 bp selected from 3' (5') mRNA untranslated region of Tra-2 or its ortholos is used to create miRNA construct. Either rtTA or tTS can be used in conjunction with pTre-Tight or pTre-mod/U6, respectively.

We do not rule out that rtTA/pTre-Tight, tTs/pTre-mod/U6 or other regulatory systems may be exchangeable to express the RNAi systems including long dsmRNAs, shRNA or miRNA to silence Tra-2 or its orthologs in the mentioned insect species. The number of the direct repeats of a 36 bp sequence that contains the 19 bp tet operator sequence (tetO) can also be modified depend on each case to enhance tighter regulation.

Different promoters can be used for driving the RNAi systems, however, we prefer, an insect spermatogenesis promoter such as Bam-2, nanos, aly, β2 from *Drosophila*, or β2 from *Anopheles gambiae*. These promoters specifically drive the Tra-2 RNAi systems in spermatogenesis to kill X chromosome-bearing sperms, in the event that some spermatozoa survive the knockdown and fertilize eggs. We perform an additional transformation, in which an early zygote promoter (for example AaKLC2 promoter) is used to drive the rtTA/pTre-Tigh or tTs/pTre-mod/U6 system.

Some Definitions:

*Culicine* mosquitoes refer to mosquito species which have a pair of chromosomes (chromosome I) that are similar in size but are distinguishable in many species by the presence in the X (m) or absence in the Y (M) of C-banding intercalary heterochromatin[35].

Tra-2 gene sequences from Culicine mosquitoes refer to mRNA coding sequences including 5' and 3' UTR regions only[36].

The RNAi kernel sequences refer to any recombinant DNA sequence which includes two inverted repeats (IR) in conjunction with a linker or intron (loop) sequence. The sequence of the IR is derived from any part of the Culicine Tra-2 mRNA sequences.

We define Tra-2 RNAi kernel sequences as an RNAi encoding sequence, whose expression is under the control of a repressible transactivator protein system.

We define Tra-2 micro RNA sequences as an artificial miRNA using an endogenous specific miRNA backbone to carry a target sequence which is derived from 3' or 5' UTR of Tra-2 mRNA.

EXAMPLES: CREATION OF AN ALL STERILE MALE POPULATION OF INSECTS

Example 1. Creation of a Tet-on System to Express Long dsmRNA to Knockdown Tra-2 and its Homologs or Orthologs I. Components:

A schematic illustration of this construct can be seen in FIG. 1A. 1/RRM Tra-2 sequences: In these examples, we used three types of RRMs (RRM1, RRM2 and RRM3) to create Tra-2 RNAi kernel constructs. These sequences were obtained from sequencing the target species or blasting from (http://www.vectorbase.org/). Some sequences were deposited in Genbank. The accession numbers for the RRM sequences are: KJ147314; KJ147315; KJ147316; KJ147317; KJ147318; KJ147319; KJ147320; KJ14732. The invention covers the use of Tra-2 gene sequences belonging to *Aedes albopictus, Aedes aegypti, Aedes polynesiensis, Culex quinquefasciatus* or any of the other *Culicinae* mosquitoes. The other components of plasmids were identical. 2/ *Drosophila*/β2 tubulin promoter (or other insect spermatogenesis promoter): obtained by PCR from *Drosophila* DNA. 3/ Transactivator component[30] (pTet-On Advanced plasmid-rtTA): Clontech. 4/ Regulator element: pTre-tight plasmid (Cat. No. 631059)-Clontech. 5/ Reporter gene: http://piggybac.bio.nd.edu/. 6/ piggyBac plasmids: http://piggybac.bio.nd.edu/. 7/ Helper plasmid: http://piggybac.bio.nd.edu/.

II. RRMs from *Aedes albopictus* and *Aedes polynesiensis*

The RRM sequences of Tra-2 were identified from *Aedes albopictus, Aedes polynesiensis, Aedes aegypti* or other Culicinae mosquitoes (*Aedes* spp) and the details were described in Hoang and Hoang[23]. The RRM1 and RRM2 sequences are available in Genbank (KJ147314; KJ147315; KJ147316; KJ147317; KJ147318; KJ147319; KJ147320; KJ14732). This first example below shows a method used to create a DNA recombinant RNAi kernel sequence which produced long dsmRNAs by using the Tra-2 RRM sequences and to construct it under a Tet-On regulatory system.

RRM1 DNA sequence
(SEQ ID NO: 3)
5'AGTAAGTGCCTCGGTGTGTTCGGCCTAAGCAGCTACACCAACGAAACCAGCC
TGATGGACGTTTTCGCACCGTACGGAACCATTGACAAGGCGATGATTGTCTAC
GATGCCAAGACGAAGGTTTCCCGNGGGTTCGGATTCGTGTACTTCCAGGAGCA
GAGTGCGGCCACCGAAGCCAAAATGCAGTGYAATGGNATGATGCTGCATGAG
CGCACGATTAGAGTGGATTATTCGGTGACC-3'

RRM2 DNA sequence
(SEQ ID NO: 4)
5'AGTAAGTGCCTCGGTGTGTTCGGCCTNAGYAGCTAYACCAMCGAARCCAR
CCTGATGGAYGTNTTCKCNCCGTWCGGNACCATHGACAAGGCNATGATTGT
CTACGATGCCAAGACGAAGGYNTCCCGNGGGTTYGGNTTCGTGTAYTTCCAG
GAGCAGAGTKCGGCCACNGARGCCAAAMTGCAGTGYAAYGGAATGRWRCT
GCAYGAGCGNACGATTAGAGTGGATTATTCGGTGACC-3'

RRM1 amino acid sequence
(SEQ ID NO: 5)
  1  -S--K--C--L--G--V--F--G--L--S--S--Y--T--N--E--T--S--L--M--D-
 21  -V--F--A--P--Y--G--T--I--D--K--A--M--I--V--Y--D--A--K--T--K-
 41  -V--S--R--G--F--G--F--V--Y--F--Q--E--Q--S--A--A--T--E--A--K-
 61  -M--Q--C--N--G--M--M--L--H--E--R--T--I--R--V--D--Y--S--V--T-

RRM2 amino acid sequence
(SEQ ID NO: 6)
  1  -S--K--C--L--G--V--F--G--L--S--S--Y--T--T--E--T--N--L--M--D-
 21  -V--F--S--P--F--G--T--I--D--K--A--M--I--V--Y--D--A--K--T--K-
 41  -A--S--R--G--F--G--F--V--Y--F--Q--E--Q--S--S--A--T--E--A--K-
 61  -L--Q--C--N--G--M--E--L--H--E--R--T--I--R--V--D--Y--S--V--T-

(Underlined region indicates the region selected for primers. Bold and underline character indicates nucleotide DNA and amino acid substitutions, respectively). Two fragments of 135 bp from the bottom parts (3') of these RRM1 and RRM2 regions were used to assemble Tra-2 RNAi constructs. Because the sequences of RRM1 and RRM2 are only different in some regions, primers derived from sequences outside of those regions were used for amplifying both RRMs. PCR was carried out in a 25 µl reaction: 2.5 µl PCR buffer; 1.5 µl MgCL (25 mM); 0.5 µl dNTPs (10 mM); each primer 0.5 µl (10 pmol/µl); 0.15 µl Taq DNA polymerase (5 U/µl); and 10-40 ng DNA template. The thermal profile of PCR was [94° C./4; (94° C./30"; 59° C./30"; 72° C./45")×3; (94° C./30"; 57° C./30"; 72° C./45")×3; (94° C.130"; 54° C./30"; 72° C./45")×35; 72° C./10'].

1-(BA-EX1F)
(SEQ ID NO: 7)
5'CGATCTCGGATCCATGCCAAGACGAAGGTTTCCCGAG 3'

2-(X-Ex1R)
(SEQ ID NO: 8)
5'CGGCAATGACCTCGAGACCGGTCACCGAATAATCCACTCAA 3'

3-(SAL-EX1F)
(SEQ ID NO: 9)
5'GGCGTCAATGTCGACATGCCAAGACGAAGGTTTCCCGAG 3'

4-(ECORI-EX1R)
(SEQ ID NO: 10)
5'CGGACGTTGGAATTCGACGGTCACCGAATAATCCACTCAA 3'

Primers 1 & 3, and 2 & 4, are similar forward and reverse primers, respectively. A combination of 1&2 would produce the same PCR product as that using 3 and 4. The only differences in those PCR products are the endonuclease restriction enzyme sequences inserted in the front parts (5') of the primers (underline). This allows for the PCR products to be ligated to an intron or linker that contains the same restriction sites in a desired orientation. If a connection between the two inverted repeats was a linker about 10 bp, PCR reactions to amplify these fragments used the same reverse primer (2 or 4) and therefore the products contained the same restriction sites at the 3' end (XhoI or EcoRI). Two PCR products were inversely connected after XhoI or EcoRI enzyme treatments, however, if an intron was inserted between the two inverted repeats, it required the use of both inverse primers. Two PCR products had different sticky ends at the 3' end (XhoI and EcoRI) and were easily ligated with an intron that ends with XhoI and EcoRI restriction sites. In this invention, any linker or intron sequence from any insect can be used in conjunction with the two inverted repeats, provided that the nucleotides GT and AG are inserted at both the start and the end of those sequences, respectively. These are recognition signals for intron splicing sites. After two identical DNA fragments were reversely connected via an intron or linker, these RNAi kernel sequences (1 &2) were ligated into the transactivator system in a desired orientation provided that the trans-activator plasmids contain the same restriction sites.

III. RRM from *Culex quinquefasciatus*

The RRM sequences of Tra-2 were identified from genomic sequences of *Culex quinquesfaciatus* that are available in the Vectorbase website (http://www.vectorbase.org/). The method/process for amplifying this sequence in *Culex quinquesfaciatus*, or from other *Culex* spp was described in Hoang and Hoang[23].

RRM3 DNA sequence
(SEQ ID NO: 11)
CGTAACGGAATAGTCCACCCGGATGGTTCGCTCGTGCATTACCATTCCGTTGCA

CTGCACCTTGGCTGCGGAAGCGTCCTCCAGGTTGACAAAGTACACGAATCCGA

ACCCGCGGGACGCCTTCGTCTTGGCATCGTACACGATCTGCACCTTCTCGATCA

-continued

```
ATCCGAACCGGCCAAACACGGTCCTCAGGTCCGCCTCCTGGGTGTAATTGCTG

AGGCCAAACACGCCGAGGCAGGTCGA
```

RRM3 amino acid sequence (SEQ ID NO: 12)

```
 1-S--T--C--L--G--V--F--G--L--S--N--Y--T--Q--E--A--D--L--R--T-

21-V--F--G--R--F--G--L--I--E--K--V--Q--I--V--Y--D--A--K--T--K-

41-A--S--R--G--F--G--F--V--Y--F--V--N--L--E--D--A--S--A--A--K-

61-V--Q--C--N--G--M--V--M--H--E--R--T--I--R--V--D--Y--S--V--T-
```

In *Culex quinquesfaciatus* the whole RRM3 sequence was used to create an RNAi kernel sequence as the nucleotide sequences at the 3' and 5' end are both appropriate for the design of suitable primers. 24 bp at the start and 22 bp at the end of RRM3 (underlined) were used to create a pair of primers. These primers were used to amplify the Tra-2 RRM 240 bp region of the other *Culex* spp, even such distant species as *Culex vishnue, Culex pipiens* or *Culex tritaeniorhynchus* using similar conditions. Using the same PCR conditions, a 240 bp band was amplified, among other bands. A gel extraction step was performed for the 240 bp band using Qiagen columns. The DNA elution is diluted 10-20 times in water and 1 μl used as template for the same PCR. A specific 240 bp band was amplified and used to assemble Tra-2 RNAi constructs for the respective species.

7-(BA-EX1F)

(SEQ ID NO: 13)
5' CGATCTCGGATCCCGTAACGGAATAGTCCACCCGGAT 3'

8-(X-Ex1R)

(SEQ ID NO: 14)
5' CGGCAATGACCTCGAGACTCGACCTGCCTCGGCGTGTTTG 3'

9-(SAL-EX1F)

(SEQ ID NO: 15)
5' GGCGTCAATGTCGACCGTAACGGAATAGTCCACCCGGAT 3'

10-(ECOR1-EX1R)

(SEQ ID NO: 16)
5' CGGACGTTGGAATTCGATCGACCTGCCTCGGCGTGTTTG 3'

PCR was carried out in a 25 μl reaction: 2.5 μl PCR buffer; 1.5 μl MgCL (25 mM); 0.5 μl dNTPs (10 mM); 0.5 μl each primer (10 pmol/μl); 0.15 μl Taq DNA polymerase (5 U/μl); 10-40 ng DNA template. Thermal profile of PCR was [94° C./4; (94° C./30"; 59° C./30"; 72° C./45")×3; (94° C./30"; 57° C./30"; 72° C./45")×3; (94° C./30"; 54° C./30"; 72° C./45")×35; 72° C./10']. Afterward, these PCR products were processed in the same manner as that outlined in the example above of *Aedes albopictus, Aedes aegypti* and *Aedes polynesiensis*. These fragments were connected by a linker or intron, and after this RNAi kernel sequence (3) was constructed, it was ligated into the trans-activator plasmids to transform *Culex quinquesfaciatus* embryos.

IV. Connection of the RNAi Kernel Structures (Long dsmR-NAs) with pTre-Tight Repressor The pTre-tight plasmid (Cat. No. 631059) from Clontech was mixed with the RNAi kernel sequence (1 or 2 or 3) in 1:3 molar ratio in a 30 μl reaction in the presence of BamHI and SalI restriction enzymes. After digestion, ligation was performed by adding T4 ligation plasmid into the denatured restriction enzyme mixture. The circle plasmid was transformed into competent cells (DH5α™ derivative, New England Biolabs), isolated and cultured overnight to harvest a larger amount of plasmid DNA from each clone. The size of the new plasmid was 2556 kb plus the size of the RNAi kernel sequence. In the case of RRM1 and RRM2 from *Aedes albopictus, Aedes aegypti* and *Aedes polynesiensis*, only 135 bp of each RRM was used, the plasmid size was about 3026 bp if using an intron of 200 bp. If a linker of 10 bp was used, the plasmid was about 2826 bp. In the case of *Culex quinquesfaciatus*, the whole 240 bp was used, and so if it was accompanied with 200 bp intron, the fragment size was 3236 bp. If a linker of 10 bp was used, the plasmid was about 3046 bp. A fragment including the Tre operator and the RNAi kernel sequence (tetOx7+PminCMV+RNAi kernel sequence+SV40 polyA) was amplified by two primers which contain HindIII and Acc65I restriction sites. These sites were then available for ligation with the piggyBac plasmid and the other parts of the construct.

(Tre-HindIII)

(SEQ ID NO: 17)
CGATCTAAGCTTCTCGAGTTTACTCCCTATCAGTGA (Tre-Ace65I)

(SEQ ID NO: 18)
CGATCTGGTACCAGTCAGTGAGCGAGGAAGCTCGAG

PCR was carried out in a 25 μl reaction: 2.5 μl PCR buffer; 1.5 μl MgCL (25 mM); 0.5 μl dNTPs (10 mM); 0.5 μl each primer (10 pmol/μl); 0.15 μl Taq DNA polymerase (5 U/μl); and 10-40 ng DNA template. The thermal profile of PCR was [94° C./4; (94° C./90"; 54° C./60"; 72° C./3 min 30")×35; 72° C./10']. The PCR products amplified from the RRMs of *Aedes albopictus* and *Aedes polynesiensis* with a 10 bp linker was 875 bp, meanwhile a 200 bp intron produced 1065 bp products. The PCR products amplified from the RRM of *Culex quinquesfaciatus* were 1085 bp and 1275 bp, including a 10 bp linker or 200 bp intron, respectively. The PCR products were digested by Acc65I and HindIII and purified by Qiagen columns. The product was then available for a final ligation.

V. Connection of the *Drosophila* β2 Spermatogenesis Specific Promoter with a Trans-Activator Sequence The *Drosophila* β2 tubulin promoter sequence was obtained from GenBank or http://flybase.org/reports/FBgn0003889.html. Sequences of other insect spermatogenesis specific promoter could be found from Genbank, vectorbase or flybase. We prefer endogenous promoters to be used for a target species if available. Two primers which contain EcoRI and Apa I digestion sites were designed from the sequence. These primers amplify 230 bp of 5'UTR of the β2 tubulin gene from *Drosophila* genomic DNA. The thermal profile of PCR is [94° C./4; (94° C./30"; 55° C./30"; 72° C./45")×35; 72° C./10'].

β2-ApaI-F (SEQ ID NO: 19)
CGATCTGGGCCCGGAAATCGTAGTAGCCTATTTGTGA

β2-EcoRI-R (SEQ ID NO: 20)
CGGACGTTGGAATTCCCTGAATGTGTACAATTTCACGCAT

The pTet-On Advanced plasmid (Clontech, Catalog No. 630930) was digested using two restriction enzymes, EcoRI and HindIII, producing a band of 1222 bp. This DNA fragment was then ligated to the β2 tubulin promoter sequence via the EcoRI restriction site to produce a fragment of 1458 bp. rtTA protein production was then controlled by the β2 tubulin spermatogenesis specific promoter. The ligation product was digested using ApaI and purified by Qiagen columns. The product was then available for a final ligation.

VI. Whole Plasmid Assembles.

The pXL-BacII-ECFP plasmid from http://piggybac.bio.nd.edu/ was used to assemble all the above fragments into completed Tra-2 RNAi constructs. The pXL-BacII-ECFP plasmid carried a 3×P3 promoter which drives an ECFP reporter gene. This reporter gene is expressed in a tissue specific manner under the control of the 3×P3 promoter. Mosquitoes were transformed with this marker and mosquito eyes would be fluoresced a cyan color. The pXL-BacII-ECFP plasmid was digested using ApaI and Acc65I and purified by Qiagen columns. The linear plasmid was 5390 bp. The plasmid was then mixed with Tre fragments (III, Example 1), and the β2+rtTA fragment (IV, Example 1) in 1:3:3 molar ratio. T4 ligation plasmid was added into a 30 µl reaction. The ligation product was used to transform into competent cells. Ligation products were in a range of different sizes as follows: For *Aedes albopictus*, *Aedes aegypti* and *Aedes polynesiensis*, two plasmids containing a 10 bp linker or a 200 bp intron were 7723 bp and 7913 bp in size, respectively. Meanwhile, plasmids for *Culex quinquesfaciatus* were 7933 bp and 8123 bp for a 10 bp linker and a 200 bp intron, respectively.

Example 2. Creation of a Tet-on System to Express shRNA and Knockdown Tra-2 or its Homologs or Orthologs A schematic illustration of this construct can be seen in FIGS. 1C, D & E.

I. Components:

In the case where the knockdown effect was induced by a shRNA construct, there were two options of the tetO-operator segments (pTre-tight or pTre-mod/U6) and two trans-activator systems (rtTA-advanced or tTS) used respectively for controlling the expression. 1/Tra-2 gene sequences: In these examples, we used Tra-2 coding gene sequences to create shRNA. These sequences were obtained from sequencing Tra-2 cDNA of target species or blasting from (http://www.vectorbase.org/). Some sequences, we deposited in Genbank. The accession numbers for the RRM sequences are: KJ147314; KJ147315; KJ147316; KJ147317; KJ147318; KJ147319; KJ147320; KJ14732. The invention covers the use of Tra-2 gene sequences belonging to *Aedes albopictus*, *Aedes polynesiensis*, *Culex quinquefasciatus* or any of the other Culicine mosquitoes. The other components of plasmids were identical. 2/ *Drosophila* β2 tubulin promoter (or other insect spermatogenesis promoter): obtained by PCR from *Drosophila* DNA. 3/ Trans-activator component with two options (rtTA or tTS): Clontech. 4/ Regulator element with two options: pTre-tight plasmid (Cat. No. 631059) or pTre-moci/U6 (Cat. No. 630925), Clontech. 5/ Reporter gene: http://piggybac.bio.nd.edu/. 6/ piggyBac plasmids: http://piggybac.bio.nd.edu/. 7/ Helper plasmid: http://piggybac.bio.nd.edu/.

II. Ligation with the pTre-Tight System

In the case where the rtTA/pTre-tight system was used, a 19-28 bp selected sequence of a short RNA derived from Tra-2 mRNA, not including 5' and 3' UTR, could be selected to form a shRNA oligo. In fact, 19 bp of the sense (GTCTACGATGCCAAGACGA) from position $340^{th}$ to $358^{th}$ of AAEL004293-RA gene (Tra-2 RRM1) in supercont1.113 of *Aedes aegypti* was used to create a short mRNA ending by an 8 bp poly A track as the terminator. The loop (underline) was used as Mcintyre G J and Fanning GC[37]. The short mRNA sequence was [GTCTACGATGCCAAGACGATTCAAGAGATCGTCTTGGCATCGTAGACTTTTTTT] (SEQ ID NO: 21). Two primers for this hairpin were Sh1-BamHI-F [GCCGCGGGATCCGTCTACGATGCCAAGACGATTCAAGAGATCGTCTTGGCAT] (SEQ ID NO: 22) and Sh2-SalI-R [GCCGCGGTCGACAAAAAAAAGTCTACGATGCCAAGACGAGATGAGGTCG] (SEQ ID NO: 23). In its entirety the short hairpin was 55 bp including polyA. This PCR product was Qiagen purified and mixed in 3:1 ratio with the pTre-tight plasmid and digested by BamHI and SalI. A T4 ligation step produced a re-circled 2616 bp plasmid. A fragment of 412 bp including the Tre operator and the shRNA sequence (tetOx7+PminCMV+shRNA) was amplified from the plasmid by two primers which contain HindIII and Acc65I restriction sites. These sites were then available for ligation with the piggyBac plasmid and the other parts of the construct.

(Tre-HindIII)

(SEQ ID NO: 24)
CGATCTAAGCTTCTCGAGTTTACTCCCTATCAGTGA (Tre-Acc65I)

(SEQ ID NO: 25)
CGATCTGGTACCGTCGACAAAAAAAAGTCTACGATG

PCR was carried out in a 25 µl reaction: 2.5 µl PCR buffer; 1.5 µl MgCL (25 mM); 0.5 µl dNTPs (10 mM); 0.5 µl each primer (10 pmol/µl); 0.15 µl Taq DNA polymerase (5 U/µl); and 10-40 ng DNA template. The thermal profile of PCR was [94° C./4; (94° C./15"; 54° C./10"; 72° C./30")×35; 72° C./10']. The PCR products were digested by Acc65I and HindIII and purified by Qiagen columns. The product was then available for a final ligation.

III. Ligation with the pTre-Mod/U6 System

In the case where tTS/pTre-mod/U6 system was used, the mammal U6 promoter of the plasmid was replaced by a minimal U6 promoter from *Ae. aegypti*. The *D. melanogaster* U6snRNA gene sequence (GenBank accession no. NR002083) was used in a BLAST search to identify putative U6snRNA genes in the *Ae. Aegypti*. An U6 ortholog was found in Supercont1.287:1096905-1097016 (AAGE02013372.1). The forward primers were redesigned to include an NdeI restriction site upstream of 54 bp minimal promoter containing promoter core sequence and TATA box [GTAGAAGACTATATAAGAGCAGAGGCAAGAGTAGTGAAATGTCTTTGCTTCGGCGTCTACGATGCCAAGACGATTCAAGAGATCGTCTTGGCATCGTAGACTTTTTTTT](SEQ ID NO: 26). The primer were Sh1-NdeI-F [GCCGCGCATATGGTAGAAGACTATATAAGAGCAGAGGCAAGAGTAGTGAAATGTCT TTGCTTCGGC GTCTACGATGCCAAGACGATT-CAAGAGATCGTCTTGGCAT] (SEQ ID NO: 27) and the reverse contained a BemHI site. Sh2-BamHI-R [GCCGCGGGATCCAAAAAAAAGTCTACGATGCCAA-GACGAGATGAGGTCG] (SEQ ID NO: 28). The PCR product was digested with BamHI and SalI to produce a 121 bp fragment. The pSIREN-RetroQ-TetH Vector (Cat. No. 630925, Clontech) was digested by NdeI and BamHI to remove the mammal U6 promoter and re-circled by the 121 bp fragment containing Aedes minimal U6 and short hairpin above. This plasmid was PCR with two primers, TetR-HindIII-F [CGATCTAAGCTTCTTTCGTCTTCACTT-GAGTTTACTCCCTA] (SEQ ID NO: 29) and TetR-Acc65I-R [CGATCTGGTACCGGATCCAAAAAAAAGTCTAC-GATGCCAAGACGAG] (SEQ ID NO: 30) and produced a 416 bp fragment containing Tet-R Operator+Aedes U6 minimal promoter +shRNA. This fragment was available for a final ligation to transcriptional suppressor (tTS).

IV. Connection of the *Drosophila* β2 Spermatogenesis Specific Promoter with a pTet-on Transactivator (rtTA) or Transcriptional Suppressor (tTS)

This step was similar to those mentioned in Example 1(IV) in the case where rtTA was used. For the tTS system, the reverse primer of *Drosophila* β2 tubulin promoter sequence needed to contain an XbaI restriction site. Two primers which contained XbaI and Apa I digestion sites were designed from the β2 sequence. These primers amplified 230 bp fragment of 5'UTR of the β2 tubulin gene from *Drosophila* genomic DNA. The thermal profile of PCR were [94° C./4; (94° C./20"; 55° C./15"; 72° C./30")×35; 72° C./10'].

β2-ApaI-F
(SEQ ID NO: 31)
CGATCTGGGCCCGGAAATCGTAGTAGCCTATTTGTGA

β2-XbaI-R
(SEQ ID NO: 32)
CGGACGTCTAGACATCCTGAATGTGTACAATTTCACGCAT

The tTS plasmid (Clontech, Catalog No. 630925) was digested using two restriction enzymes, XbaI and HindIII, producing a band of 2021 bp. This DNA fragment was then ligated to the β2 tubulin promoter sequence via the XbaI restriction site to produce a fragment of 2257 bp. tTS protein production was then controlled by the β2 tubulin spermatogenesis specific promoter. The ligation product was digested using ApaI and purified by Qiagen columns. The product was then available for a final ligation.

V. Whole plasmid assembles.

This step was performed in a similar fashion to the previous step outlined in Example 1. It required a backbone Piggybac plasmid to ligate to two operating fragments, transactivator protein and RNAi operation. The pXL-BacII-ECFP plasmid from http://piggybac.bio.nd.edu/ was used to assemble all the above fragments into completed Tra-2 shRNA constructs. The pXL-BacII-ECFP plasmid carried a 3×P3 promoter which drives an ECEP reporter gene. The pXL-BacII-ECFP plasmid was digested using ApaI and Acc65I and purified by Qiagen columns. The linear plasmid was 5390 bp. The plasmid was then mixed with pTre-tight fragments (I, Example 2), and the β2+rtTA fragment (III, Example 2) in 1:3:3 molar ratio. In the other case with tTS system, the Piggybac plasmid was then mixed with pTre-mod/U6 fragments (II, Example 2) and the β2+tTS fragment (III, Example 2) in 1:3:3 molar ratio. T4 ligation plasmid was added into a 30 µl reaction. The ligation product was used to transform into competent cells. Ligation products were in a range of different sizes as follows:

For the rtTA system, the shRNA constructed in the Piggybac plasmid was finally 7248 bp. Meanwhile, tTS system produced a product of 8063 bp. This was a shRNA system for knocking down Tra-2 gene in *Aedes*. We did not perform the construction for *Culex quinquesfaciatus* as an example here, however the principal is identical.

Example 3. Creation of a Tet-on System to Express miRNA and Knockdown Tra-2 or its Homologs or Orthologs A schematic illustration of this construct can be seen in FIG. 1F.

I. Components:

In the case where the knockdown effect was induced by a miRNA construct, there were two options of the tetO-operator segments (pTre-tight or pTre-mod/U6) and two trans-activator systems (rtTA-advanced or tTS) used respectively for controlling the expression. 1/Tra-2 gene sequences: In these examples, we used Tra-2 3'UTR sequences to create miRNA [SEQUENCE ID.No1]. These sequences were obtained from sequencing Tra-2 cDNA of target species to use Marathon or RACE kits. The invention covers the use of 3' or 5' UTR of mRNA Tra-2 sequences belonging to *Aedes albopictus, Aedes polynesiensis, Culex quinquefasciatus* or any of the other Culicine mosquitoes. The other components of plasmids were identical. 2/ *Drosophila* β2 tubulin promoter (or other insect spermatogenesis promoter): obtained by PCR from *Drosophila* DNA. 3/ Transactivator component with two options (rtTA or tTS): Clontech. 4/ Regulator element with two options: pTre-tight plasmid (Cat. No. 631059) or pTre-mod/U6 (Cat. No. 630925), Clontech. 5/Reporter gene: http://piggybac.bio.nd.edu/. 6/ piggyBac plasmids: http://piggybac.bio.nd.edu/. 7/ Helper plasmid: http://piggybac.bio.nd.edu/.

II. Artificial miRNAs Creation

Artificial miRNAs were built from a miRNA backbone. We selected miRNAs in the same miRNA group shared between *Drosophila* and mosquitoes but their specific expression in *Aedes* males. The backbone of any miRNA male specific expression in Culicine mosquitoes can be used to create artificial miRNAs. We do not rule out the possibility to use a miRNA backbone from other animal to knockdown Tra-2 gene, because miRNAs are extremely conserved across taxa. The 22 bp sequence corresponding to mature aae-mir-932 was replaced with sequences perfectly complementary to sequences from the Tra-2 mRNA 3'UTR, generating two new miRNAs, aae-mir-932-mir-Tra-2. 1 and aae-mir-932-mir-Tra-2. 2. Different sites in the Tra-2 mRNA transcript are targeted to minimize a secondary structure which would prevent the miRNA-RISC complex from being able to bind and cleave the mRNA. The use of several miRNAs targeting a common transcript, but at different positions, also limits the possibility that a single mutational event (in either the miRNA or the target sequence) will result in a loss of knockdown efficacy. *Aedes* microRNA mir-932 was found in http://www.mirbase.org/ and the mature sequence was used to search on Vectorbase. The whole sequence was found in supercont1.1064:154096-154190; gene: AAEL017875. We targeted two sites, each of 22 bp in 3'UTR of an *Aedes* Tra-2 male specific mRNA (Sequence ID 1). The target sequences are GCGATTCAAACTAAACAT-TTTA (SEQ ID NO: 33) and GATCGTGTGGTTAT-CAAATGTC (SEQ ID NO: 34). For the first target site, two primers were designed.

Mi-932-F1.1

(SEQ ID NO: 35)
[CCATAGTACTGACGAAAGATAGCCGTTTCTGTAATCAT
AGAATAGCTGCGATTCAAACTAAACATTTTATGTGCTTTAGACGAAC]
and Mi-932-R1.1

(SEQ ID NO: 36)
[CTGGTATCAATCACACTTGAGATTGTTGATGATCATTGAGAATCGGC
GATTCAAACTAAACATTTTAGTTCGTCTAAAGCACA].

GTCTAAAGCACA](SEQ ID NO: 36). Two primers were PCR by annealing each other to fill in two 3' ends and produce a 152 bp fragment. For the second target site, two primers were designed.

Mi-932-F1.2

(SEQ ID NO: 37)
[CCATAGTACTGACGAAAGATAGCCGTTTCTGTAATCATAGAATAGCTGA
TCGTGTGGTTATCAAATGTCTGTGCTTTAGACGAAC]
and Mi-932-R1.2

(SEQ ID NO: 38)
[CTGGTATCAATCACACTTGAGATTGTTGATGATCATTGAGAATCGGATC
GTGTGGTTATCAAATGTCGTTCGTCTAAAGCACA].

Two primers were also annealed to each other to produce a 152 bp fragment. The thermal profile of PCRs was [94° C./4; (94° C./10"; 55° C./5"; 72° C./15")×35; 72° C./10']. These fragments were used as templates to amplify two bigger fragments by two pairs of primers containing further sequence of mi-932 at 5' and 3' direction. This strategy enhanced the efficiency of an artificial miRNA when it had a longer flanking sequence. The first primer pair for the initial fragment had the same restriction site in reverse primer to those in the forward primer of the second pair. This was used to connect two fragments, each containing a target sequence to form a miRNA molecule having two hairpin loops. The first extended fragment did not contain a poly A. The lengths of the fragments were 304 and 334 bp.

Mi-932-F2.1-Bam (SEQ ID NO: 39)
CGATCTCGGATCCCCTATCTTAAAATATAAACTAATCAAACGAATAGTGA
TCACCAGAGCATTACCTAAAAAATGTTGAGAAATTTTCCATAGTACTGAC
GAAAGATAG

Mi-932-R2.1-Eco-RI (SEQ ID NO: 40)
CGGACGTTGGAATTCGTGTTGCCATGTCATCATTTTTTGTTGAACATCCA
CTGACTGGCGTTTATCGATTGTCATTCACTTCTGGTATCAATCACACTT

Mi-932-F2.1-Eco-RI (SEQ ID NO: 41)
CGGACGTTGGAATTCCCTATCTTAAAATATAAACTAATCAAACGAATAGT
GATCACCAGAGCATTACCTAAAAAATGTTGAGAAATTTTCCATAGTACTG
ACGAAAGATAG

Mi-932-R2.1-SalI
(SEQ ID NO: 42)
GGCGTCAATGTCGACTGACTCCATTCCATTTTCTTTTTGTTCCTCGTGTT
GCCATGTCATCATTTTTTGTTGAACATCCACTGACTGGCGTTTATCGATT
GTCATTCACTTCTGGTATCAATCACACTT.

PCR was carried out in a 25 µl reaction: 2.5 µl PCR buffer; 1.5 µl MgCL (25 mM); 0.5 µl dNTPs (10 mM); 0.5 µl each primer (10 pmol/µl); 0.15 µl Taq DNA polymerase (5 U/µl); and 10-40 ng DNA template. The thermal profile of PCR was [94° C./4; (94° C./15"; 55° C./10"; 72° C./30")×35; 72° C./10].
III. Ligation with the pTre-Tight System
Two 304 and 334 bp fragments containing different miRNA targets were mixed with BamHI, EcoRI and SalI and purified by a Qiagen column. T4 ligation was performed and the 632 bp fragment was ligated to BamHI/EcoRI digested pTre-tight plasmid and produced 3203 bp circled plasmid. In fact, we needed only the fragment of tetOx7+PminCMV+miRNA, therefore the plasmid sequence was used as a template to amplify a 1017 bp fragment by two primers which contain HindIII and Acc65I restriction sites. These sites were then available for ligation with the piggyBac plasmid and the other parts of the construct.

(Tre-HindIII)

(SEQ ID NO: 43)
CGATCTAAGCTTCTCGAGTTTACTCCCTATCAGTGA (Tre-Acc65I)

(SEQ ID NO: 44)
CGATCTGGTACCTGACTCCATTCCATTTTCTTTTTGTTCCTCGTGTTG

PCR was carried out in a 25 µl reaction: 2.5 µl PCR buffer; 1.5 µl MgCL (25 mM); 0.5 µl dNTPs (10 mM); 0.5 µl each primer (10 pmol/µl); 0.15 µl Taq DNA polymerase (5 U/µl); and 10-40 ng DNA template. The thermal profile of PCR was [94° C./4; (94° C./20"; 54° C./45", 72° C./60")×35; 72° C./10']. The PCR products were digested by Acc65I and HindIII and purified by Qiagen columns. The product was then available for a final ligation.
IV. Ligation with the pTre-Mod/U6 System
The use of the pTre-mod/U6 system required to replace the U6 mammal promoter by Aedes minimal one as mentioned in Example 2 (II). The forward primers were re-designed to include an NdeI restriction site upstream of 54 bp minimal promoter containing promoter core sequence and TATA box and the PCR produced a 686 bp fragment. The primer were miR1-NdeI-F (SEQ ID NO: 45)
[GCCGCGCATATGGTAGAAGACTATATAAGAGCAGAGGCAAGAGTAGTG
AAATGTCTTTGCTTCGGCCCTATCTTAAAATATAAACTAATC]

and the reverse contained a BamHI site.
miR2-BamHI-R [GCCGCGGGATCCTGACTCCATTC-CATTTTCTTTTTGTTCC TCGTGTTG] (SEQ ID NO: 46). The RNAi-Ready pSIREN-RetroQ-TetH Vector (Cat. No. 630925) was digested by NdeI and BamHI to remove the mammal U6 promoter and re-circled by the 686 bp fragment containing Aedes minimal U6 and artifcial miRNA with two loops. This plasmid was PCR with two primers, TetR-HindIII-F [CGATCTAAGCTTCTTTCGTCTTCACTT-GAGTTTACTCCCTA](SEQ ID NO: 47) and TetR-Acc65I-R [CGATCTGGTACCTGACTCCATTCCAT-TTTCTTTTTGTTCCTC GTGTTG] (SEQ ID NO: 48) and produced a 969 bp fragment containing Tet-R Operator +Aedes U6 minimal promoter +miRNA. This fragment was available for a ligation to transcriptional suppressor (tTS).
V. Connection of the Drosophila β2 Spermatogenesis Specific Promoter with a pTet-on Transactivator (rtTA) or Transcriptional Suppressor (tTS)
This step was identical to those mentioned in Example 2(III). Two transactivator systems (rtTA and tTS) were prepared under a spermatogenesis specific promoter and then were available for ligations.
VI. Whole Plasmid Assembles.
The pXL-BacII-ECFP plasmid from http://piggybac.bio.nd.edu/is used to assemble all the above fragments into completed Tra-2 miRNA constructs. The pXL-BacII-ECFP plasmid carries a 3×P3 promoter which drives an ECEP reporter gene. This reporter gene would be expressed in a tissue specific manner under the control of the 3×P3 promoter.

The pXL-BacII-ECFP plasmid is digested using ApaI and Acc65I and purified by Qiagen columns. The linear plasmid is 5390 bp. The plasmid is then mixed with PTre-tight fragments (Example 3, II), and the β2+rtTA fragment (Example 3, IV) in 1:3:3 molar ratio. In the other case with tTS system, the Piggybac plasmid was then mixed with pTre-mod/U6 fragments (III, Example 3), and the β2+tTS fragment (IV, Example 3) in 1:3:3 molar ratio. T4 ligation plasmid is added into a 30 µl reaction. The ligation product is used to transform competent cells. Ligation products are expected in a range of different sizes as follows:

For the rtTA system, the miRNA constructed in the Piggybac plasmid was finally 7853 bp. Meanwhile, tTS system produced a product of 8604 bp. This was a miRNA system for knocking down Tra-2 gene in *Aedes*. We did not perform the construction for *Culex quinquesfaciatus* as an example here. However, the principal is identical.

Example 4. Adaptation of Early Zygote Promoter to Express RNAi and Knockdown Tra-2 or its Homologs or Orthologs A schematic illustration of this construct can be seen in FIG. 1B.

This method was performed when X chromosome-bearing sperms were not completely eradicated, few percentages of female might survive. The early zygote promoter would help to kill the female zygotes in embryos or early stages. This type of promoter could be adapted into both rtTA or tTS systems and those systems can be used to regulate the expression of long mRNAs, shRNA or miRNA. Any insect early zygote specific-promoter can be used in this case. We used *Ae. aegypti*-AaKLC2.1 promoter[29] (AAEL011410-RA) to drive the expression of transactivator protein. In the case of using rtTA, we used two restriction sites are ApaII in the forward and EcoRI in reverse primer.

```
AAKLC2.12-APAI-F
                                  (SEQ ID NO: 49)
CGATCTGGGCCCATATGAAAATTGTTATGAAGAAA

AAKLC2.1-ECORI-R
                                  (SEQ ID NO: 50)
CGGACGTTGGAATTCTGTTGATTGATTGGAAGATTTGGAA
```

Meanwhile, the tTS required a XbaI restriction site in the reverse primer.

```
AAKLC2.1-APAI-F
                                  (SEQ ID NO: 51)
CGATCTGGGCCCATATGAAAATTGTTATGAAGAAA

AAKLC2.1-XBAI-R
                                  (SEQ ID NO: 52)
CGGACGTCTAGATGTTGATTGATTGGAAGATTTGGAA.
```

This promoter can be adapted to the long, dsmRNA interference construct or the shRNA of Tra-2 gene. However, it cannot be adapted to the specific miRNA mentioned above because the aae-mir-932 is male specific for adult stages.

Example 5. Overexpression of Tra-2 Gene

A schematic illustration of this construct can be seen in FIG. 1G.

We also used a method to silence Tra-2 by gene overexpression this technique was performed simply by cloning the whole Tra-2 cDNA male-specific, including 3' and 5' UTR [SEQUENCE ID.No 1]. This fragment was ligated to CMV minimal promoter within the pTre-tight plasmid and inserted into the Piggybac plasmid together with rtTa fragment. In this case: the Tra-2 male specific cDNA could be used together with SV40 polyA 3'UTR which was available in the plasmid. This gene was induced by the presence of Dox and resulting in overexpression.

Example 6. Plasmid Injection and Transformant Selection

The Tra-2 RNAi plasmid (long DsRNA (siRNA), shRNAs or miRNA) or Tra-2 overexpression construct was mixed with a pBSII-IE1-orf (http://piggybac.bio.nd.edu/) helper plasmid. The helper produced transposase enzyme which helps piggyBac in the Tra-2 RNAi plasmid jump into the mosquito genome. A suitable concentration of the injection mixture would be 600 ng of the Tra-2 RNAi plasmid plus 400 ng of the helper plasmid per micro liter (µl) of 1× phosphate buffer. Mosquito embryos were injected into the posterior end within 2 hours after oviposition. After 4 days post injection, the eggs were submerged into deoxygenized water. $G_0$ survivors were kept to cross with wild type males or females. $G_1$ larvae were screened under a stereo fluorescent microscope; any fluorescent larva found was deemed to be transformant and were crossed to build a transformed line. Such lines were tested in Dox conditions to check for an effect on the sex ratio to express a gene by Tet-on, using 10 to 30 mg Dox per litter. Any line which exhibited a skew towards males (over 80% in Tet-on conditions) was kept for further analysis and potentially for vector control applications. Those lines were the confirmed as genetic sexing strains (GSS).

Example 7. Doxycycline Induces Tra-2 Knockdown in Transient Experiments

In this example, we show the transient expression of a Tra-2 RNAi construct which created long dsmRNAs. The detail method to create this construct was described in Example 4. The promoter driving rtTA protein was AaKLC2.1. In the presence of doxycycline (Dox), Tet-On Advanced binds to the tetracycline response element in pTre-tight, and produces high-level tran-scription of the downstream gene. *Ae. aegypti* strain (Hanoi1) was fed on blood containing three different Dox concentrations to produce eggs containing different Dox doses (mg/litre). The construct named AaKLC2.1-long-02 after Maxiprep purification was diluted in $1^x$ injection buffer at 1.6 µg/µl. Embryos were desiccated briefly in 50 sec and stuck into a plastic cover slip via a piece of double sticky tape. The Voltalef oil was used to cover the embryos. After injection, the cover slip was then immediately transferred into a cover slip staining rack which was kept in a sealed plastic box with 100% humidity at 27° C. for 3-4 days and then hatched in Dox deoxygenated water. 500 embryos were injected in each Dox concentration. Larvae were reared under standard conditions. Three different Dox concentrations which were equivalent to the concentrations in blood meals were added to the rearing water. The sex ratio among survivors of each Dox concentration were shown in the below table.

TABLE 1

Long dsmRNA construct injection and female lethality induced by different Dox concentrations.

| Ae.aegypti (Hanoi1) | 0.3 mg of Dox/L (%) | 3 mg of Dox/L (%) | 30 mg of Dox/L (%) |
|---|---|---|---|
| Hatched rate | 122/500 (24.4) | 93/500 (18.6) | 74/500 (14.8) |
| Sex ratio | 58♂/53♀ (52.3/47.7) | 54♂/33♀ (62.1/37.9) | 51♂/5♀ (91.1/8.9) |

Example 8. Wolbachia Transinfection

After Tra-2 genetic sexing strains (GSS) are established they can be used as materials for Wolbachia infection. The simplest way to achieve this is to cross males of a GSS with Wolbachia infected females from a CI strain. Many such mosquito lines (which can induce up to 100% CI) were established[28,29]. After a Tra-2 knockdown/Wolbachia line is established, the males of the line need to be tested by crossing with females from a target population to obtain an exact CI level. Based on the result, a control strategy could be drawn. In our case such lines were not available but a trans-infection can be performed as our method which is described below: Mosquito or Drosophila eggs from desired Wolbachia infected lines were collected at 70 or 30 minutes after oviposition, respectively. 500-1000 eggs were homogenized in 20 ml homogenizing buffer [(250 mM sucrose, 90 mM potassium chloride, 30 mM sodium chloride, 15 mM magnesium sulfate, 5.5 mM calcium chloride, 0.1% [wt/vol] Lubrol; ICN Inc., Costa Mesa, Calif.)][39]. The homogenate was filtered through a 0.95 µm pore size and centrifuged at 150×g for 10 min to remove egg cover debris. Then the suspension containing Wolbachia was pelleted at 5,000 g for 10 min. The pellet was re-suspended in homogenizing buffer. One to two day old female Ae. albopictus recipients were anaesthetized and microinjected directly in the thorax with Eppendorf femtotips II glass needles with manual break tips. The virgin females were kept between 20 to 22° C. This temperature slowed down the multiplication of Wolbachia and significantly increased survival rate of the injected females. The females were mated to uninfected males the next day to establish isofemale lines. Once the females laid eggs, they were PCR tested for the presence of Wolbachia using universal wsp primers 81F and 691R[38]. F 1 males were PCR with the same primers for checking trans-infection of the line.

Example 9. Adult Female Transinfection and Dox Challenge

Ae. albopictus strains (Hanoi 1 and Laos2) were trans-infected with Wolbachia from a Drosophila line (Oregon-R). This fly carries wMel Wolbachia. Drosophila embryos were collected as mentioned above. 1-2 day old virgin females were anaesthetized and microinjected directly in the thorax. Table 2 shows results of two injections. These lines were maintained at a standard condition and challenged with the presence of Dox (30 mg/L) in 4-5 days from the third larvae to 3 day old adults. They were PCR re-tested for the presence of Wolbachia after the challenge using universal wsp primers 81F and 691R[38].

TABLE 2

Wolbachia trans-infection into female adults

| | Number of injected females | Survival number | Survivor laid eggs | Isofemale contained Wolbachia |
|---|---|---|---|---|
| Ae.albopictus Hanoi 1 | 251 | 15 | 9 | 1 |
| Ae.albopictus Laos2 | 270 | 21 | 14 | 1 |

TABLE 3

Wolbachia trans-infection lines and Dox challenge.

| | $3^{rd}$-$4^{th}$ larvae (on Dox) | Pupae | 3 day old adult (on Dox) | 81F/691R PCR test |
|---|---|---|---|---|
| wMel/Ae.albopictus Hanoi 1 | 50 | 50 | 49 | 49 (100%) |
| wMel/Ae.albopictus Laos2 | 50 | 50 | 50 | 50 (100%) |

Example 10

The Ae. aegypti strain named Hanoi1 was transformed with a Tra-2 RNAi (long dsmRNA) construct. This construct was assembled with rtTA(pTet-on advanced) and pTre-tight regulatory system as mentioned in Example 1. The strain was challenged with Dox three different concentrations (0.3 mg/L; 3 mg/L and 30 mg/L) between the third larvae stage and 3 day old adult. The males from each Dox concentration challenge were divided into two groups; one group was Q-PCR to reveal the knockdown level of Tra-2. The other group was outcrossed with wild type females. Total RNA from Hanoi 1 wild type males and Tra-2 RNAi/Hanoi 1 transgenic males were isolated in pools of 5 males in 3 biological replicates. The primers used for Actin5C (endogenous reference gene) were F: (5'-ATCGTACGAACTTCCCGATG-3') (SEQ ID NO: 53) and R: (5'-ACAGATCCTTTCGGATGTCG-3') (SEQ ID NO: 54) which produced a 125 bp fragment. Primers used for amplifying Tra-2, which produced a 125 bp fragment nearby the Tra-2 RNAi target site, were: Forward: (5' AGCGAAA-CATCGGCCTGTTCATC 3') (SEQ ID NO: 55) and Reverse: (5' AGGCTGGTTTCGTTGGTGTAGC 3') (SEQ ID NO: 56). Three biological replicates were carried out in each Dox condition. The knockdown of expression levels were calculated by the relative standard curve method (Applied Biosystems), in which Act5C as an endogenous reference and wild type Hanoi 1 as an exogenous calibrator. PCR cycle was 95° C. for 15 mins; 45 cycles of 10 sec at 95° C., 10 sec at XC, 20 sec at 72° C., plate reading. X is annealing temperature, of which 59° C. for the reference gene Actin5C and 55° C. was used for Tra-2 primers. FIG. 1 showed expression levels of Tra-2 in males which had been induced in three different Dox concentrations. 0.3 mg/L caused a slight difference in comparison with wild type (96.98% wild type). 3 mg/L induced a higher knockdown level (73.7% wild type) meanwhile 30 mg/L resulted in a highly knocked down level after 5 days treatment (33.26% wild type). See details in FIG. 2.

10 homozygous males (3 day old) from each concentration were crossed with 10 wild type virgin females. Table 4 shows the sex ratio of the crosses.

|            | Male (0.3 mg/L) | Male (3 mg/L)   | Male (30 mg/L)  |
| ---------- | --------------- | --------------- | --------------- |
| Egg        | 500             | 500             | 500             |
| Hatch rate | 477/500 (95.40) | 453/500 (90.60) | 458/500 (91.60) |
| Male ratio | 235/221 (51.53) | 279/151 (64.88) | 387/27 (93.47)  |

REFERENCES CITED

1. Knipling, E. 1955. Possibilities of insect control or eradication through use of sexually sterile males. *J Econ Entomol.* 48:459-62.
2. Reiter, P. 2007. Oviposition, dispersal and survival in *Aedes aegypti*. implications for the efficacy of control strategies. *Vector-Borne Zoonotic Dis.*7:261-73.
3. Itô, Y. 1977. A model of sterile insect release for eradication of melonfly *Dacus Cucurbitae* Coquillett. *Appl. Ent. Zool.* 12:310-312.
4. Wyss, J. H. 2000. Screwworm eradication in the Americas. *Ann. New York Acad. Sci.* 916, 186-193.
5. Benedict, M. Q and. Robinson, A. S. 2003. The first releases of transgenic mosquitoes: an argument for the sterile insect technique. *Trends in parasitology* 19.8: 349-355.
6. Strunnikov, V. A. 1979. On the prospects of using balanced sex-linked lethals for insect pest control. *Theoretical and Applied Genetics* 55.1: 17-21.
7. Strunnikov. 1983. *Control of silkworm Reproduction, Development and Sex. MIR Publishers. Moscow.*
Laven, H. 1967. Eradication of *Culex pipiens fatigans* through cytoplasmic incompatibility. *Nature* 216, 383-384.
9. O Neill, 2011. Modified arthopode and method of use. US 2011 0145939. United State, Patent application publication.
10. Dobson, S. L. 2011. Transfected mosquito vectors. U.S. Pat. No. 7,868,222 B1.
11. Ashburner, M., Hoy, M. A., Peloquin, J. J. 1998. Prospects for the genetic transformation of arthropods. *Insect Mol Biol.* 7(3):201-213.
12. DeVault, J. D., Hughes, K. J., Leopold, R. A., Johnson, O. A., & Narang, S. K. 1996. Gene transfer into corn earworm (*Helicoverpa zea*) embryos. *Genome Research,* 6(7), 571-579.
13. DeVault, J. D., K. J. Hughes, O. A. Johnson, and S. K. Narang. 1996. Biotechnology and new integrated pest management approaches. *Bio/Technology* 14: 46-49.
14. Bello, B., Resendez-Perez, D., Gehring, W. J. 1998. Spatial and temporal targeting of gene expression in *Drosophila* by means of a tetracycline-dependent transactivator system. *Development* 125:2193-2202.
15. Alphey, L. 2007. Area-Wide Control of Insect Pests: From Research to Field. Implementation, Springer, Dordrecht, The Netherlands.
16. Alphey, L. 1999. *PN*: WO 01/39599 A2.
17. Phuc, H. K., Andreasen, M. H., Burton, R. S., Vass, C., Epton, M. J., Pape, G. et al. 2007. Late-acting dominant lethal genetic systems and mosquito control. *BMC Biol.* 5, 1-11.
18. Massonnet-Bruneel, B., Corre-Catelin, Lacroix, N. R., Lees, R. S., Hoang, K. P., Nimmo, D., Alphey, L., and Paul Reiter, P. 2013. Fitness of transgenic mosquito *Aedes aegypti* males carrying a dominant lethal genetic system. *Plos One.*
19. Genewatch.2012.http://www.genewatch.org/uploads/f03c6d66a9b354535738483c1c3d4 9e4/Oxitec_unansweredQs_fin.pdf
20. Heinrich, J. C. & M. J. Scott, 2000. A repressible female-specific lethal genetic system for making transgenic insect strains suitable for a sterile-release program. *Proc. Natl. Acad. Sci. USA* 97: 8229-8232.
21. Fu, G., Lees, R. S., Nimmo, D., Aw, D., Jin, L., Gray, P., Berendonk, T., White-Cooper, H., Scaife, S., Kim, P. H. et al. 2010. Female-specific flightless phenotype for mosquito control. *Proc Natl Acad Sci USA* 107: 4550-4.
22. Bargielowski, I., Kaufmann, C., Alphey, L., Reiter, P., Koella, J. 2012. Flight Performance and Teneral Energy Reserves of Two Genetically-Modified and One Wild-Type Strain of the Yellow Fever Mosquito *Aedes aegypti*. *Vector Borne Zoonotic Diseases* 12, 1053-1058.
23. Hoang, T. D. and Hoang, K. P. 2012; PCTNN2011/000011. Culicinae mosquito Tra-RNAi, a method to genetically produce maleness populations. WIPO. http://www.sumobrain.com/patents/wipo/Culicinae-mosquito-tra-2-rna/WO2012129577.html
24. White-Cooper, H. 2012. Tissue, cell type and stage-specific ectopic gene expression and RNAi induction in the *Drosophila* testis. *Spermatogenesis,* 2(1), 11-22.
25. Stebbins, M. J., Urlinger, S., Byrne, G., Bello, B., Hillen, W., & Yin, J. C. 2001. Tetracycline-inducible systems for *Drosophila. Proc. Natl. Acad. Sci. USA,* 98(19), 10775-10780.
26. Dobson, S. L, Rattanadechakul, W. 2001. A novel technique for removing *Wolbachia* infections from *Aedes albopictus* (Diptera: Culicidae). *J Med Entomol;* 38:844-849.
27. Fry, A. J., M. R. Palmer, and D. M. Rand. 2004. Variable fitness effects of *Wolbachia* infection in *Drosophila melanogaster."* *Heredity* 93, (4) 379-389.
28. Xi, Z. Y, Khoo, C. CH, Dobson, S. L 0.2005. *Wolbachia* establishment and invasion in an *Aedes aegypti* laboratory population. *Science* 310: 326-328.
29. Blagrove, M. S C, et al. 2012. *Wolbachia* strain wMel induces cytoplasmic incompatibility and blocks dengue transmission in *Aedes albopictus. Proc. Natl. Acad. Sci. USA* 109.1. 255-260.
30. Gossen, M., & Bujard, H. 1992. Tight control of gene expression in mammalian cells by tetracycline-responsive promoters. *Proc. Natl. Acad. Sci. USA,* 89(12), 5547-5551.
31. Debra, J. T. 2013. siRNA Design Methods and Protocols. Humana Press
32. Biedler, James K., and Zhijian. T. 2010. Evolutionary analysis of the kinesin light chain genes in the yellow fever mosquito *Aedes aegypti*: gene duplication as a source for novel early zygotic genes. *BMC evolutionary biology* 10.1: 206.
33. Wang, X., Venable, J., LaPointe, P., Hutt, D. M., Koulov, A. V., Coppinger, J., . . . & Balch, W. E. 2006. Hsp90 co chaperone Aha1 down regulation rescues misfolding of CFTR in cystic fibrosis. *Cell,* 127(4), 803-815.
34. Hammond, S. M., Caudy, A. A., Hannon, G. J. 2001. Post transcriptional gene silencing by double-stranded RNA. *Nat Rev Genet;* 2: 110-119.
35. Knudson et al. 1996. 175-214. *The Biology of Disease vectors. University Press of Colorado*
36. Latchman, 1998. Gene regulation. A eukaryotic perspective. $3^{rd}$ edition. Stanley Thornes Publishers 37. Mcintyre, G. J and Fanning, G. C. 2006. Design and cloning strategies for constructing shRNA expression vectors. *BMC Biotechnol* 6:1.doi: 10.1186/1472-6750-6-1.

38. Braig, H. R., Zhou, W., Dobson, S. L. & O'Neill, S. L. 1998. Cloning and Characterization of a Gene Encoding the Major Surface Protein of the Bacterial Endosymbiont *Wolbachia pipientis J. Bacteria* 180, 2373-2378.

What is claimed is:

1. A method of producing a strain of *Culicinae* mosquito comprising the steps of:

stably transforming a *Culicinae* mosquito with a Transformer-2 (Tra-2) DNA construct comprising (1) a RNAi kernel comprising a first DNA sequence comprising at least 19 base pairs of the mosquito Tra-2 gene, wherein the mosquito is a species selected from the group consisting of *Aedes aegypti, Aedes Albopictus, Aedes polynesiensis* and *Culex quinquefasciatus;* a second DNA sequence which is an inverted repeat of the first DNA sequence; and an intron or linker DNA sequence, wherein the intron or linker DNA sequence is connected to the end of the first DNA sequence and the beginning of the second DNA sequence, wherein the transcription of the first and second DNA sequences produces single strands of mRNA with complementary sequences exposed at ends of the strands of mRNA, which form a double strand hairpin mRNA structure, (2) a tetracycline-responsive transactivator operably linked and controlling expression of the RNAi kernel sequence, which is activated only in the presence of doxycycline, (3) an early zygote promotor operably linked and controlling expression of the tetracycline-responsive transactivator during early zygote stage in the *Culicinae* mosquito, which early zygote promoter is an AaKLC2 promoter, (4) an insect spermatogenesis promoter operably linked and controlling expression of the tetracyline-responsive transactivator during spermatogenesis in the *Culicinae* mosquito, wherein the spermatogenesis promoter is selected from the group consisting of Bam-2, nano, aly, and B2 obtained from *Drosophila* or *Anopheles gambiae,* wherein the Tra-2 DNA construct is stably expressed during early zygote state in the *Culicinae* mosquito transformed therewith, so that the double strand hairpin mRNA structure produced is effective for Tra-2 gene knockdown of early female zygotes in early zygote state, and wherein the Tra-2 RNAi DNA construct is stably expressed during spermatogenesis in the *Culicinae* mosquito transformed therewith, so that the double strand hairpin mRNA structure produced knocks down the Tra-2 gene of X(m) chromosome-bearing sperms; and infecting *Culicinae* female mosquitos with at least one strain of Wolbachia bacteria so as to induce cytoplasmic incompatibility in male progeny of a *Culicinae* mosquito population breeding with said strain of *Culicinae* mosquito.

2. The method of producing a strain of *Culicinae* mosquito of claim 1, wherein the Transformer-2 (Tra-2) DNA construct further comprises an early zygote promoter operably linked and controlling expression of the tetracycline-responsive transactivator during early zygote stage in the *Culicinae* mosquito, wherein the Tra-2 RNAi DNA construct is stably expressed during early zygote stage in the *Culicinae* mosquito transformed therewith, so that the double strand hairpin mRNA structure produced knocks down the Tra-2 gene of early female zygotes in early zygote stage.

3. The method of producing a strain of *Culicinae* mosquito of claim 1, wherein the first DNA sequence Tra-2 gene is selected from the group consisting of SEQ ID NO:1, SEQ ID NO:3, SEQ ID NO:4 and SEQ ID NO:11.

4. A mosquito produced by the method of claim 1.

5. A mosquito produced by the method of claim 2.

6. A method to produce a population of *Culicinae* mosquito, comprising the steps:
   (1) producing a population of Culicinae mosquitos transformed with a plasmid comprising
      a) a RNAi kernel comprising
         a first DNA sequence comprising at least 19 base pairs of the mosquito Tra-2 gene, wherein the mosquito is a species selected from the group consisting of *Aedes aegypti, Aedes Albopictus, Aedes polynesiensis* and *Culex quinquefasciatus,*
         a second DNA sequence which is an inverted repeat of the first DNA sequence, and
         an intron or linker DNA sequence, wherein the intron or linker DNA sequence is connected to the end of the first DNA sequence and the beginning of the second DNA sequence,
         wherein the transcription of the first and second DNA sequences produces single strands of mRNA with complementary sequences exposed at ends of the strands of mRNA, which form a double strand hairpin mRNA structure,
      b) a tetracycline-responsive transactivator operably linked and controlling expression of the RNAi kernel sequence, which is activated only in the presence of doxycycline,
      c) an early zygote promotor operably linked and controlling expression of the tetracycline-responsive transactivator during early zygote stage in the *Culicinae* mosquito, which early zygote promoter is an AaKLC2 promoter, and
      d) an insect spermatogenesis promoter operably linked and controlling expression of the tetracyline-responsive transactivator during spermatogenesis in the *Culicinae* mosquito,
         wherein the spermatogenesis promoter is selected from the group consisting of Bam-2,nano, aly, and B2 obtained from *Drosophila* or *Anopheles gambiae,*
         wherein the Tra-2 DNA construct is stably expressed during early zygote state in the *Culicinae* mosquito transformed therewith, so that the double strand hairpin mRNA structure produced knocks down the Tra-2 gene of early female zygotes in early zygote state, and wherein the Tra-2 RNAi DNA construct is stably expressed during spermatogenesis in the *Culicinae* mosquito transformed therewith, so that the double strand hairpin mRNA structure produced knocks down the Tra-2 gene of X(m) chromosome-bearing sperms;
   (2) infecting female mosquitos in the population of *Culicinae* mosquitos with at least one strain of Wolbachia bacteria, which is effective to induce cytoplasmic incompatibility in male progeny of a *Culicinae* mosquito population breeding with said strain of *Culicinae* mosquito;
   (3) allowing the transformed population of *Culicinae* mosquitos to breed and produce larvae progeny;
   (4) causing the larvae progeny to ingest doxycycline so as to activate the tetracycline-responsive transactivator and knocks down the Tra-2 gene of X(m) chromosome-bearing sperms in males; and
   (5) allowing the larvae progeny to mature and breed within the population of *Culicinae* mosquitos, and produce progeny, wherein the progeny form a population of *Culicinae* mosquitos.

7. The method to produce a population of *Culicinae* mosquito of claim 6, wherein the Transformer-2 (Tra-2) DNA construct further comprises an early zygote promoter operably linked and controlling expression of the tetracycline-responsive transactivator during early zygote stage in the *Culicinae* mosquito,
   wherein the Tra-2 RNAi DNA construct is stably expressed during early zygote stage in the *Culicinae* mosquito transformed therewith, so that the double strand hairpin mRNA structure produced knocks down the Tra-2 gene of early female zygotes in early zygote stage, and
   wherein in step (4) the doxycycline activates tetracycline-responsive transactivator during early zygote stage, and knocks down the Tra-2 gene of early female zygotes in early zygote stage so as to kill female mosquitos in an embryo or larvae stage in step (5).

8. The method to produce a population of *Culicinae* mosquito of claim 6, wherein the first DNA sequence Tra-2 gene is selected from the group consisting of SEQ ID NO:1, SEQ ID NO:3, SEQ ID NO:4 and SEQ ID NO:11.

9. A method for controlling a mosquito population, comprising the steps of:
   (1) producing a population of *Culicinae* mosquitos transformed with a plasmid comprising
      a) a RNAi kernel comprising
         a first DNA sequence comprising at least 19 base pairs of the mosquito Tra-2 gene, wherein the mosquito is a species selected from the group consisting of *Aedes aegypti, Aedes Albopictus, Aedes polynesiensis* and *Cules quinquefasciatus,*
         a second DNA sequence which is an inverted repeat of the first DNA sequence, and
         an intron or linker DNA sequence, wherein the intron or linker DNA sequence is connected to the end of the first DNA sequence and the beginning of the second DNA sequence,
         wherein the transcription of the first and second DNA sequences produces single strands of mRNA with complementary sequences exposed at ends of the strands of mRNA, which form a double strand hairpin mRNA structure,
      b) a tetracycline-responsive transactivator operably linked and controlling expression of the RNAi kernel sequence, which is activated only in the presence of doxycycline,
      c) an early zygote promotor operably linked and controlling expression of the tetracycline-responsive transactivator during early zygote stage in the *Culicinae* mosquito, which early zygote promoter is an AaKLC2 promoter, and
      d) an insect spermatogenesis promoter operably linked and controlling expression of the tetracyline-responsive transactivator during spermatogenesis in the *Culicinae* mosquito,
   wherein the spermatogenesis promoter is selected from the group consisting of Bam-2, nano, aly, and B2 obtained from *Drosophila* or *Anopheles gambiae,*
   wherein the Tra-2 DNA construct is stably expressed during early zygote state in the *Culicinae* mosquito transformed therewith, so that the double strand hairpin mRNA structure produced knocks down the Tra-2 gene of early female zygotes in early zygote state, and
   wherein the Tra-2 RNAi DNA construct is stably expressed during spermatogenesis in the *Culicinae* mosquito transformed therewith, so that the double strand hairpin mRNA structure produced knocks down the Tra-2 gene of X(m) chromosome-bearing sperms;

(2) infecting female mosquitos in the population of *Culicinae* mosquitos with at least one strain of Wolbachia bacteria, which is effective to induce cytoplasmic incompatibility in male progeny of a *Culicinae* mosquito population breeding with a wild-type strain of *Culicinae* mosquito;

(3) allowing the transformed population of *Culicinae* mosquitos to breed and produce larvae progeny;

(4) causing the larvae progeny to ingest doxycycline so as to activate the tetracycline-responsive transactivator and knocks down the Tra-2 gene of X(m) chromosome-bearing sperms in males;

(5) allowing the larvae progeny to mature and breed within the population of *Culicinae* mosquitos, and produce progeny, wherein the progeny form a population of *Culicinae* mosquitos; and (6) releasing the progeny of step (5) into a natural habitat of a population of wild-type *Culicinae* mosquitos, under conditions that breeding occurs between the progeny and the wild-type *Culicinae* mosquitos and the population of wild-type *Culicinae* mosquitos is controlled thereby.

10. The method of claim 9, wherein the Transformer-2 (Tra-2) DNA construct further comprises an early zygote promoter operably linked and controlling expression of the tetracycline-responsive transactivator during early zygote stage in the *Culicinae* mosquito, wherein the Tra-2 RNAi DNA construct is stably expressed during early zygote stage in the *Culicinae* mosquito transformed therewith, so that the double strand hairpin mRNA structure produced is effective for Tra-2 gene knockdown of early female zygotes in early zygote stage, and wherein in step (4) the doxycycline activates tetracycline-responsive transactivator during early zygote stage, and knocks down the Tra-2 gene in early female zygotes in early zygote stage so as to kill female mosquitos in an embryo or larvae stage in step (5).

11. The method of claim 9, wherein the first DNA sequence Tra-2 gene is selected from the group consisting of SEQ ID NO:1, SEQ ID NO:3, SEQ ID NO:4 and SEQ ID NO:11.

12. The method of claim 9, wherein the wild-type *Culicinae* mosquitos are *Aedes aegypti* mosquitos.

13. The method of claim 9, wherein in step (5) the progeny form a population comprising at least 90% male Culicinae mosquitos.

14. The method of claim 6, wherein in step (5) the progeny form a population comprising at least 90% male *Culicinae* mosquitos.

* * * * *

SEQUENCE LISTING

<160> NUMBER OF SEQ ID NOS: 56

<210> SEQ ID NO 1
<211> LENGTH: 754
<212> TYPE: DNA
<213> ORGANISM: Aedes aegypti

<400> SEQUENCE: 1

```
caagacgaag gtttcccgag ggttcggatt cgtgtacttc caggaacaga gtgcgaccac      60
cgaagccaaa atgcagtgta atggaatgat gctgcatgag cgcacgatta gagtggatta     120
ttcggtgacc gaaagaccgc atacgcccac gcccggtgtc tacatgggag ctagaagcac     180
tgagaaacgg aagcaccgca gttcctatag ctacaggaga cggagctatg atgacgatta     240
ccatcatcgg cggtcaagac gcagcagatc tcgttcctgt catcatcacc gtagatctag     300
tcatcgccat caccatcgac gtgaccgtgc tcgtgatcgt tctccatctt attcctcagt     360
tgactcacgt cgatcctatc gataatgtgc tagaaggatt gtgttttga cgtaagtcat     420
cttttttcaag acctcacgaa gaccctacaa acaaagaagt tcaagtcaag tattattgaa     480
gatagaatct gtatcagtaa aaactattct tcaaatgaca caagggaaga acagattact     540
cttcattaat ccaagggtaa attgtatgta gctaaccgtt ctgtttttct tttcgtttca     600
ggatgtttgg atttcttcac attttagaga actagttttc attattccgc gattcaaact     660
aaacatttta tttatttatt agttaaagat cgtgtggtta tgaaatgtcg tttgtgcaac     720
cattaaccaa aaataaggga ttgctaaaaa aaaa                                 754
```

<210> SEQ ID NO 2
<211> LENGTH: 757
<212> TYPE: DNA
<213> ORGANISM: Aedes aegypti

<400> SEQUENCE: 2

```
tgccaagacg aaggtttccc gtgggttcgg attcgtgtac ttccaggagc agagtgcggc      60
caccgaagcc aaaatgcagt gcaatgggat gatgctgcat gagcgcacga ttagagtgga     120
ttattcggtg accgaaagac cgcatacgcc cacgcccggt gtctacatgg gagctagaag     180
cactgagaaa cagaagcacc gcagttccta tagctacagg agacggagct atgatgacga     240
ttaccatcat cggcggtcaa gacgcagcag atctcgttcc tgtcatcacc atcgtagatc     300
tagtcatcac catcgccatc gacgtgaccg tgctcgtgat cgttctccat cttattcctc     360
agttgactca cgtcgatcct atcgataatg tgctagaagg attgtgtttt tgatgtaagt     420
catcttttc aagacctcac gaagaccta caaacaaaga agttcacgtc aagtattatt     480
gaagatagaa tctgtatcag taaaaactac tcttcaaatg acacaaggga agaacagatt     540
actcttcatt aatccaaggg taaatcatat gtagctaacc gatctgtttt tcttttcgtt     600
tcaggatgtt tggatttctt cacattttag agaactagtt tcatggttc cgcgattcaa     660
actaaacatt ttatttattt attagtaaaa gatcgtgtgg ttatgaaatg tcgtttgggc     720
aaccattaac caaaataag ggattgctaa aaaaaaa                               757
```

<210> SEQ ID NO 3
<211> LENGTH: 240

```
<212> TYPE: DNA
<213> ORGANISM: Aedes aegypti
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (195)..(195)
<223> OTHER INFORMATION: a, c, t, g, unknown or other

<400> SEQUENCE: 3
agtaagtgcc tcggtgtgtt cggcctaagc agctacacca acgaaaccag cctgatggac    60
gttttcgcac cgtacggaac cattgacaag gcgatgattg tctacgatgc caagacgaag   120
gtttcccgng ggttcggatt cgtgtacttc caggagcaga gtgcggccac cgaagccaaa   180
atgcagtgya atggnatgat gctgcatgag cgcacgatta gagtggatta ttcggtgacc   240

<210> SEQ ID NO 4
<211> LENGTH: 240
<212> TYPE: DNA
<213> ORGANISM: Aedes sp.
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (138)..(138)
<223> OTHER INFORMATION: a, c, t, g, unknown or other
<220> FEATURE:
<221> NAME/KEY: modified_base
<222> LOCATION: (171)..(171)
<223> OTHER INFORMATION: a, c, t, g, unknown or other
<220> FEATURE:
<221> NAME/KEY: modified_base
<222> LOCATION: (213)..(213)
<223> OTHER INFORMATION: a, c, t, g, unknown or other

<400> SEQUENCE: 4
agtaagtgcc tcggtgtgtt cggcctnagy agctayacca mcgaarccar cctgatggay    60
gtnttckcnc cgtwcggnac cathgacaag gcnatgattg tctacgatgc caagacgaag   120
gyntcccgng ggttygqntt cgtgtayttc caggagcaga gtkcggccac ngargccaaa   180
mtgcagtgya ayggaatgrw rctgcaygag cgnacgatta gagtggatta ttcggtgacc   240

<210> SEQ ID NO 5
```

<211> LENGTH: 80
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 5

Ser Lys Cys Leu Gly Val Phe Gly Leu Ser Ser Tyr Thr Asn Glu Thr
1               5                   10                  15

Ser Leu Met Asp Val Phe Ala Pro Tyr Gly Thr Ile Asp Lys Ala Met
            20                  25                  30

Ile Val Tyr Asp Ala Lys Thr Lys Val Ser Arg Gly Phe Gly Phe Val
        35                  40                  45

Tyr Phe Gln Glu Gln Ser Ala Ala Thr Glu Ala Lys Met Gln Cys Asn
    50                  55                  60

Gly Met Met Leu His Glu Arg Thr Ile Arg Val Asp Tyr Ser Val Thr
65                  70                  75                  80

<210> SEQ ID NO 6
<211> LENGTH: 80
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 6

Ser Lys Cys Leu Gly Val Phe Gly Leu Ser Ser Tyr Thr Thr Glu Thr
1               5                   10                  15

Asn Leu Met Asp Val Phe Ser Pro Phe Gly Thr Ile Asp Lys Ala Met
            20                  25                  30

Ile Val Tyr Asp Ala Lys Thr Lys Ala Ser Arg Gly Phe Gly Phe Val
        35                  40                  45

Tyr Phe Gln Glu Gln Ser Ser Ala Thr Glu Ala Lys Leu Gln Cys Asn
    50                  55                  60

Gly Met Glu Leu His Glu Arg Thr Ile Arg Val Asp Tyr Ser Val Thr
65                  70                  75                  80

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 7
cgatctcgga tccatgccaa gacgaaggtt tcccgag                          37

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 8
cggcaatgac ctcgagaccg gtcaccgaat aatccactca a                     41

<210> SEQ ID NO 9
<211> LENGTH: 39

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggcgtcaatg tcgacatgcc aagacgaagg tttcccgag                              39

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggacgttgg aattcgacgg tcaccgaata atccactcaa                             40

<210> SEQ ID NO 11
<211> LENGTH: 240
<212> TYPE: DNA
<213> ORGANISM: Culex quinquefasciatus

<400> SEQUENCE: 11
cgtaacggaa tagtccaccc ggatggttcg ctcgtgcatt accattccgt tgcactgcac       60
cttggctgcg gaagcgtcct ccaggttgac aaagtacacg aatccgaacc cgcgggacgc      120
cttcgtcttg gcatcgtaca cgatctgcac cttctcgatc aatccgaacc ggccaaacac      180
ggtcctcagg tccgcctcct gggtgtaatt gctgaggcca aacacgccga ggcaggtcga      240

<210> SEQ ID NO 12
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Thr Cys Leu Gly Val Phe Gly Leu Ser Asn Tyr Thr Gln Glu Ala
1               5                   10                  15

Asp Leu Arg Thr Val Phe Gly Arg Phe Gly Leu Ile Glu Lys Val Gln
            20                  25                  30

Ile Val Tyr Asp Ala Lys Thr Lys Ala Ser Arg Gly Phe Gly Phe Val
        35                  40                  45

Tyr Phe Val Asn Leu Glu Asp Ala Ser Ala Ala Lys Val Gln Cys Asn
    50                  55                  60

Gly Met Val Met His Glu Arg Thr Ile Arg Val Asp Tyr Ser Val Thr
65                  70                  75                  80

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgatctcgga tcccgtaacg gaatagtcca cccggat                                37
```

```
<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cggcaatgac ctcgagactc gacctgcctc ggcgtgtttg                              40

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcgtcaatg tcgaccgtaa cggaatagtc cacccggat                               39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cggacgttgg aattcgatcg acctgcctcg gcgtgtttg                               39

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgatctaagc ttctcgagtt tactccctat cagtga                                  36

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgatctggta ccagtcagtg agcgaggaag ctcgag                                  36

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgatctgggc ccggaaatcg tagtagccta tttgtga                                 37

<210> SEQ ID NO 20
```

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cggacgttgg aattccctga atgtgtacaa tttcacgcat          40

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
gtctacgatg ccaagacgat tcaagagatc gtcttggcat cgtagacttt ttttt          55

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gccgcgggat ccgtctacga tgccaagacg attcaagaga tcgtcttggc at          52

<210> SEQ ID NO 23
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gccgcggtcg acaaaaaaaa gtctacgatg ccaagacgag atgaggtcg          49

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
cgatctaagc ttctcgagtt tactccctat cagtga          36

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
cgatctggta ccgtcgacaa aaaaaagtct acgatg          36

<210> SEQ ID NO 26
<211> LENGTH: 109

<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 26
gtagaagact atataagagc agaggcaaga gtagtgaaat gtctttgctt cggcgtctac    60
gatgccaaga cgattcaaga gatcgtcttg gcatcgtaga cttttttt                109

<210> SEQ ID NO 27
<211> LENGTH: 106
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 27
gccgcgcata tggtagaaga ctatataaga gcagaggcaa gagtagtgaa atgtctttgc    60
ttcggcgtct acgatgccaa gacgattcaa gagatcgtct tggcat                  106

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 28
gccgcgggat ccaaaaaaaa gtctacgatg ccaagacgag atgaggtc                 48

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 29
cgatctaagc ttctttcgtc ttcacttgag tttactccct a                       41

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 30
cgatctggta ccggatccaa aaaaaagtct acgatgccaa gacgag                  46

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 31
cgatctgggc ccggaaatcg tagtagccta tttgtga                            37

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cggacgtcta gacatcctga atgtgtacaa tttcacgcat                           40

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcgattcaaa ctaaacattt ta                                              22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gatcgtgtgg ttatcaaatg tc                                              22

<210> SEQ ID NO 35
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccatagtact gacgaaagat agccgtttct gtaatcatag aatagctgcg attcaaacta     60
aacattttat gtgctttaga cgaac                                           85

<210> SEQ ID NO 36
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctggtatcaa tcacacttga gattgttgat gatcattgag aatcggcgat tcaaactaaa     60
cattttagtt c                                                          71

<210> SEQ ID NO 37
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
ccatagtact gacgaaagat agccgtttct gtaatcatag aatagctgat cgtgtggtta    60
tcaaatgtct gtgctttaga cgaac                                         85

<210> SEQ ID NO 38
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctggtatcaa tcacacttga gattgttgat gatcattgag aatcggatcg tgtggttatc    60
aaatgtcgtt cgtctaaagc aca                                           83

<210> SEQ ID NO 39
<211> LENGTH: 109
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgatctcgga tccctatct taaaatataa actaatcaaa cgaatagtga tcaccagagc     60
attacctaaa aaatgttgag aaattttcca tagtactgac gaaagatag              109

<210> SEQ ID NO 40
<211> LENGTH: 99
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cggacgttgg aattcgtgtt gccatgtcat cattttttgt tgaacatcca ctgactggcg    60
tttatcgatt gtcattcact tctggtatca atcacactt                          99

<210> SEQ ID NO 41
<211> LENGTH: 111
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cggacgttgg aattccctat cttaaaatat aaactaatca acgaatagt gatcaccaga     60 gcattaccta aaaaatgttg agaaattttc catagtactg acgaaagata g            111

<210> SEQ ID NO 42
<211> LENGTH: 129
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggcgtcaatg tcgactgact ccattccatt ttcttttgt tcctcgtgtt gccatgtcat     60
cattttttgt tgaacatcca ctgactggcg tttatcgatt gtcattcact tctggtatca   120
``` atcacactt                                                              129

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgatctaagc ttctcgagtt tactccctat cagtga                                 36

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgatctggta cctgactcca ttccattttc tttttgttcc tcgtgttg                    48

<210> SEQ ID NO 45
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccgcgcata tggtagaaga ctatataaga gcagaggcaa gagtagtgaa atgtctttgc       60
ttcggcccta tcttaaaata taaactaatc                                        90

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gccgcgggat cctgactcca ttccattttc tttttgttcc tcgtgttg                    48

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgatctaagc ttctttcgtc ttcacttgag tttactccc                              39

<210> SEQ ID NO 48
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 48
cgatctggta cctgactcca ttccattttc tttttgttcc tcgtgttg                    48

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgatctgggc ccatatgaaa attgttatga agaaa                                  35

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cggacgttgg aattctgttg attgattgga agatttggaa                             40

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cgatctgggc ccatatgaaa attgttatga agaaa                                  35

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cggacgtcta gatgttgatt gattggaaga tttggaa                                37

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atcgtacgaa cttcccgatg                                                   20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
```

```
acagatcctt tcggatgtcg                                              20

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agcgaaacat cggcctgttc atc                                          23

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aggctggttt cgttggtgta gc                                           22
```